(12) United States Patent
Goble et al.

(10) Patent No.: US 6,234,178 B1
(45) Date of Patent: May 22, 2001

(54) ELECTROSURGICAL INSTRUMENT

(75) Inventors: Nigel Mark Goble, Cardiff; Colin Charles Owen Goble, Penarth, both of (GB)

(73) Assignee: Gyrus Medical Limited, Cardiff (GB)

( * ) Notice: Subject to any disclaimer, the term of this patent is extended or adjusted under 35 U.S.C. 154(b) by 0 days.

(21) Appl. No.: 09/321,207

(22) Filed: May 27, 1999

Related U.S. Application Data

(62) Division of application No. 08/740,258, filed on Oct. 25, 1996, now Pat. No. 6,013,076.

(30) Foreign Application Priority Data

| Jan. 9, 1996 | (GB) | 9600354 |
|---|---|---|
| Sep. 11, 1996 | (GB) | 9619015 |
| Sep. 25, 1996 | (GB) | 9619999 |

(51) Int. Cl.[7] ............................................ A61B 19/00
(52) U.S. Cl. ..................... 128/898; 606/41; 607/105
(58) Field of Search ............................ 606/32–34, 41, 606/42, 45–50; 407/100–105; 604/22, 114

(56) References Cited

U.S. PATENT DOCUMENTS

| Re. 33,925 | 5/1992 | Bales et al. |
|---|---|---|
| 164,184 | 6/1875 | Kidder . |
| 1,366,756 | 1/1921 | Wappler . |
| 1,735,271 | 11/1929 | Groff . |
| 1,814,791 | 7/1931 | Ende . |
| 1,889,609 | 11/1932 | Mutscheller . |
| 1,932,258 | 10/1933 | Wappler . |
| 1,943,543 | 1/1934 | McFadden . |
| 1,952,617 | 3/1934 | Wappler . |
| 1,983,669 | 12/1934 | Kimble . |

(List continued on next page.)

FOREIGN PATENT DOCUMENTS

| 243478 | 7/1946 | (CH) . |
|---|---|---|
| 651428 | 9/1937 | (DE) . |
| 1007960 | 5/1957 | (DE) . |
| 2222820 | 11/1973 | (DE) . |

(List continued on next page.)

OTHER PUBLICATIONS

Cook, Albert M. & John G. Webster, *Therapeutic Medical Devices Application and Design*, Prentice–Hall Inc., New Jersey, 1982, p. 349.

Pearce, John A., *Electrosurgery*, John Wiley & Sons Inc., New York, 1986, pp. 17, 69–75 and 87.

Wyeth, G.A., *Electrosurgical Unit*, pp. 1180–1202.

Everest Medical Technologies, Inc., "Everest Bipolar Laparoscopic Cholecystectomy," Transcript of Lecture by Dr. Olsen, Oct. 7, 1991.

Dobbie, A.K., "The Electrical Aspects of Surgical Diathermy," Biomedical Engineering, May 1969, pp. 206–216.

Valleylab, Excerpts from Valleylab SSE2L Instruction Manual, Valleylab Part No. A 945 110 005 H, Jan. 6, 1983.

(List continued on next page.)

*Primary Examiner*—Michael Peffley
(74) *Attorney, Agent, or Firm*—Nixon & Vanderhye P.C.

(57) ABSTRACT

An electrosurgical instrument is disclosed for the treatment of tissue in the presence of an electrically-conductive fluid. The instrument comprises an instrument shaft, and a tissue treatment electrode at one end of the shaft, the tissue treatment electrode being constructed to define a plurality of pockets for trapping electrically-conductive fluid. Alternatively, the tissue treatment electrode is made from an electrically-conductive material and is coated with a resistive inert material which is effective to increase the local power density within the tissue treatment electrode.

9 Claims, 5 Drawing Sheets

U.S. PATENT DOCUMENTS

| | | |
|---|---|---|
| 2,050,904 | 8/1936 | Trice . |
| 2,056,377 | 10/1936 | Wappler . |
| 2,196,171 | 4/1940 | Arnesen . |
| 2,888,928 | 6/1959 | Seiger . |
| 3,035,580 | 5/1962 | Guiorguiev . |
| 3,460,539 | 8/1969 | Anhalt, Sr. . |
| 3,595,239 | 7/1971 | Petersen . |
| 3,601,126 | 8/1971 | Estes . |
| 3,614,414 | 10/1971 | Gores . |
| 3,648,001 | 3/1972 | Anderson et al. . |
| 3,685,518 | 8/1972 | Beurle et al. . |
| 3,699,967 | 10/1972 | Anderson . |
| 3,707,149 | 12/1972 | Hao et al. . |
| 3,801,766 | 4/1974 | Morrison, Jr. . |
| 3,815,604 | 6/1974 | O'Malley et al. . |
| 3,845,771 | 11/1974 | Vise . |
| 3,847,153 | 11/1974 | Weissman . |
| 3,870,047 | 3/1975 | Gonser . |
| 3,885,569 | 5/1975 | Judson . |
| 3,898,991 | 8/1975 | Ikuno et al. . |
| 3,901,242 | 8/1975 | Storz . |
| 3,902,494 | 9/1975 | Haberlen et al. . |
| 3,903,891 | 9/1975 | Brayshaw . |
| 3,920,021 | 11/1975 | Hiltebrandt . |
| 3,920,022 | 11/1975 | Pastor . |
| 3,923,063 | 12/1975 | Andrews et al. . |
| 3,929,137 | 12/1975 | Gonser et al. . |
| 3,939,839 | 2/1976 | Curtiss . |
| 3,945,375 | 3/1976 | Banko . |
| 3,963,030 | 6/1976 | Newton . |
| 3,964,487 | 6/1976 | Judson . |
| 3,970,088 | 7/1976 | Morrison . |
| 3,974,833 | 8/1976 | Durden, III . |
| 4,011,872 | 3/1977 | Komiya . |
| 4,016,881 | 4/1977 | Rioux et al. . |
| 4,024,467 | 5/1977 | Andrews et al. . |
| 4,033,351 | 7/1977 | Hetzel . |
| 4,040,426 | 8/1977 | Morrison, Jr. . |
| 4,043,342 | 8/1977 | Morrison, Jr. . |
| 4,051,855 | 10/1977 | Schneiderman . |
| 4,060,088 | 11/1977 | Morrison, Jr. et al. . |
| 4,069,827 | 1/1978 | Dominy . |
| 4,074,718 | 2/1978 | Morrison, Jr. . |
| 4,092,986 | 6/1978 | Schneiderman . |
| 4,114,623 | 9/1978 | Meinke et al. . |
| 4,116,198 | 9/1978 | Roos . |
| 4,119,102 | 10/1978 | LeVeen . |
| 4,126,137 | 11/1978 | Archibald . |
| 4,154,240 | 5/1979 | Ikuno et al. . |
| 4,189,685 | 2/1980 | Doss . |
| 4,200,104 | 4/1980 | Harris . |
| 4,202,337 | 5/1980 | Hren et al. . |
| 4,204,549 | 5/1980 | Paglione . |
| 4,210,152 | 7/1980 | Berry . |
| 4,228,800 | 10/1980 | Degler, Jr. et al. . |
| 4,248,231 | 2/1981 | Herczog et al. . |
| 4,271,837 | 6/1981 | Schuler . |
| 4,281,373 | 7/1981 | Mabille . |
| 4,301,802 | 11/1981 | Poler . |
| 4,326,529 | 4/1982 | Doss et al. . |
| 4,346,332 | 8/1982 | Walden . |
| 4,376,263 | 3/1983 | Pittroff et al. . |
| 4,381,007 | 4/1983 | Doss . |
| 4,416,277 | 11/1983 | Newton et al. . |
| 4,418,692 | 12/1983 | Guay . |
| 4,429,698 | 2/1984 | Bentall . |
| 4,448,198 | 5/1984 | Turner . |
| 4,474,179 | 10/1984 | Koch . |
| 4,476,862 | 10/1984 | Pao . |
| 4,492,231 | 1/1985 | Auth . |
| 4,494,541 | 1/1985 | Archibald . |
| 4,512,338 | 4/1985 | Balko et al. . |
| 4,517,976 | 5/1985 | Murakoshi et al. . |
| 4,524,770 | 6/1985 | Orandi . |
| 4,532,924 | 8/1985 | Auth et al. . |
| 4,534,347 | 8/1985 | Taylor . |
| 4,548,207 | 10/1985 | Reimels . |
| 4,559,943 | 12/1985 | Bowers . |
| 4,559,951 | 12/1985 | Dahl et al. . |
| 4,562,838 | 1/1986 | Walker . |
| 4,565,200 | 1/1986 | Cosman . |
| 4,567,890 | 2/1986 | Ohta et al. . |
| 4,580,557 | 4/1986 | Hertzmann . |
| 4,590,934 | 5/1986 | Malis et al. . |
| 4,593,691 | 6/1986 | Lindstrom et al. . |
| 4,617,927 | 10/1986 | Manes . |
| 4,657,015 | 4/1987 | Irnich . |
| 4,658,819 | 4/1987 | Harris et al. . |
| 4,658,820 | 4/1987 | Klicek . |
| 4,669,468 | 6/1987 | Cartmell et al. . |
| 4,674,499 | 6/1987 | Pao . |
| 4,681,122 | 7/1987 | Winters et al. . |
| 4,682,596 | 7/1987 | Bales et al. . |
| 4,688,569 | 8/1987 | Rabinowitz . |
| 4,696,668 | 9/1987 | Wilcox . |
| 4,706,667 | 11/1987 | Roos . |
| 4,709,698 | 12/1987 | Johnston et al. . |
| 4,712,544 | 12/1987 | Ensslin . |
| 4,727,874 | 3/1988 | Bowers et al. . |
| 4,735,201 | 4/1988 | O'Reilly . |
| 4,769,005 | 9/1988 | Ginsburg et al. . |
| 4,781,175 | 11/1988 | McGreevy et al. . |
| 4,799,480 | 1/1989 | Abraham et al. . |
| 4,800,899 | 1/1989 | Elliott . |
| 4,802,476 | 2/1989 | Noerenberg et al. . |
| 4,805,616 | 2/1989 | Pao . |
| 4,813,429 | 3/1989 | Eshel et al. . |
| 4,820,298 | 4/1989 | Leveen et al. . |
| 4,823,791 | 4/1989 | D'Amelio et al. . |
| 4,827,927 | 5/1989 | Newton . |
| 4,832,048 | 5/1989 | Cohen . |
| 4,850,353 | 7/1989 | Stasz et al. . |
| 4,860,744 | 8/1989 | Johnson et al. . |
| 4,878,493 | 11/1989 | Pasternak et al. . |
| 4,886,074 | 12/1989 | Bisping . |
| 4,919,129 | 4/1990 | Weber, Jr. et al. . |
| 4,920,978 | 5/1990 | Colvin . |
| 4,931,047 | 6/1990 | Broadwin et al. . |
| 4,936,281 | 6/1990 | Stasz . |
| 4,936,301 | 6/1990 | Rexroth et al. . |
| 4,936,310 | 6/1990 | Engstrom et al. . |
| 4,936,842 | 6/1990 | D'Amelio et al. . |
| 4,943,290 | 7/1990 | Rexroth et al. . |
| 4,950,267 | 8/1990 | Ishihara et al. . |
| 4,955,377 | 9/1990 | Lennox et al. . |
| 4,966,597 | 10/1990 | Cosman . |
| 4,967,765 | 11/1990 | Turner et al. . |
| 4,969,885 | 11/1990 | Farin . |
| 4,976,711 | 12/1990 | Parins et al. . |
| 4,994,069 | 2/1991 | Ritchart et al. . |
| 4,998,933 | 3/1991 | Eggers et al. . |
| 5,007,908 | 4/1991 | Rydell . |
| 5,009,656 | 4/1991 | Reimels . |
| 5,013,312 | 5/1991 | Parins et al. . |
| 5,019,076 | 5/1991 | Yamanashi et al. . |
| 5,035,696 | 7/1991 | Rydell . |
| 5,037,379 | 8/1991 | Clayman et al. . |
| 5,047,026 | 9/1991 | Rydell . |
| 5,047,027 | 9/1991 | Rydell . |
| 5,057,107 | 10/1991 | Parins et al. . |
| 5,062,031 | 10/1991 | Flachenecker et al. . |

| Patent Number | Date | Inventor |
|---|---|---|
| 5,071,418 | 12/1991 | Rosenbaum . |
| 5,080,660 | 1/1992 | Buelna . |
| 5,083,565 | 1/1992 | Parins . |
| 5,085,659 | 2/1992 | Rydell . |
| 5,088,997 | 2/1992 | Delahuerga et al. . |
| 5,098,431 | 3/1992 | Rydell . |
| 5,099,840 | 3/1992 | Goble et al. . |
| 5,108,391 | 4/1992 | Flachenecker et al. . |
| 5,108,407 | 4/1992 | Geremia et al. . |
| 5,117,978 | 6/1992 | Blumenfeld et al. . |
| 5,122,138 * | 6/1992 | Manwaring ............................ 606/46 |
| 5,133,365 | 7/1992 | Heil, Jr. et al. . |
| 5,158,561 | 10/1992 | Rydell et al. . |
| 5,167,658 | 12/1992 | Ensslin . |
| 5,167,659 | 12/1992 | Ohtomo et al. . |
| 5,171,255 | 12/1992 | Rydell . |
| 5,171,311 | 12/1992 | Rydell et al. . |
| 5,178,620 | 1/1993 | Eggers et al. . |
| 5,190,517 | 3/1993 | Zieve et al. . |
| 5,195,959 | 3/1993 | Smith . |
| 5,196,007 | 3/1993 | Ellman et al. . |
| 5,197,963 | 3/1993 | Parins . |
| 5,201,743 | 4/1993 | Haber et al. . |
| 5,207,675 | 5/1993 | Canady . |
| 5,211,625 | 5/1993 | Sakurai et al. . |
| 5,217,457 | 6/1993 | Delahuerga et al. . |
| 5,217,458 | 6/1993 | Parins . |
| 5,217,459 | 6/1993 | Kamerling . |
| 5,221,281 | 6/1993 | Klicek . |
| 5,244,462 | 9/1993 | Delahuerga et al. . |
| 5,249,585 | 10/1993 | Turner et al. . |
| 5,250,047 | 10/1993 | Rydell . |
| 5,257,990 | 11/1993 | Nash . |
| 5,258,006 | 11/1993 | Rydell et al. . |
| 5,259,395 | 11/1993 | Li . |
| 5,261,906 | 11/1993 | Pennino et al. . |
| 5,267,994 | 12/1993 | Gentelia et al. . |
| 5,267,997 | 12/1993 | Farin et al. . |
| 5,277,201 | 1/1994 | Stern . |
| 5,277,696 | 1/1994 | Hagen . |
| 5,281,213 | 1/1994 | Milder et al. . |
| 5,281,216 | 1/1994 | Klicek . |
| 5,282,799 | 2/1994 | Rydell . |
| 5,282,845 | 2/1994 | Bush et al. . |
| 5,290,282 | 3/1994 | Casscells . |
| 5,290,283 | 3/1994 | Suda . |
| 5,300,068 | 4/1994 | Rosar et al. . |
| 5,300,069 | 4/1994 | Hunsberger et al. . |
| 5,300,070 | 4/1994 | Gentelia et al. . |
| 5,304,214 | 4/1994 | DeFord et al. . |
| 5,306,238 | 4/1994 | Fleenor . |
| 5,317,155 | 5/1994 | King . |
| 5,318,563 | 6/1994 | Malis et al. . |
| 5,320,627 | 6/1994 | Sorensen et al. . |
| 5,330,470 | 7/1994 | Hagen . |
| 5,330,471 | 7/1994 | Eggers . |
| 5,334,193 | 8/1994 | Nardella . |
| 5,334,198 | 8/1994 | Hart et al. . |
| 5,336,222 | 8/1994 | Durgin, Jr. et al. . |
| 5,342,357 | 8/1994 | Nardella . |
| 5,342,391 | 8/1994 | Foshee et al. . |
| 5,344,428 | 9/1994 | Griffiths . |
| 5,352,222 | 10/1994 | Rydell . |
| 5,354,296 | 10/1994 | Turkel . |
| 5,366,443 | 11/1994 | Eggers et al. . |
| 5,370,645 | 12/1994 | Klicek et al. . |
| 5,370,675 | 12/1994 | Edwards et al. . |
| 5,372,596 | 12/1994 | Klicek et al. . |
| 5,382,247 | 1/1995 | Cimino et al. . |
| 5,383,874 | 1/1995 | Jackson et al. . |
| 5,383,876 | 1/1995 | Nardella . |
| 5,383,917 | 1/1995 | Desai et al. . |
| 5,383,923 | 1/1995 | Webster, Jr. . |
| 5,395,363 | 3/1995 | Billings et al. . |
| 5,395,368 | 3/1995 | Ellman et al. . |
| 5,403,311 | 4/1995 | Abele et al. . |
| 5,419,767 | 5/1995 | Eggers et al. . |
| 5,422,567 | 6/1995 | Matsunaga . |
| 5,423,808 | 6/1995 | Edwards et al. . |
| 5,423,809 | 6/1995 | Klicek . |
| 5,423,810 | 6/1995 | Goble et al. . |
| 5,423,811 | 6/1995 | Imran et al. . |
| 5,431,649 | 7/1995 | Mulier et al. . |
| 5,437,662 | 8/1995 | Nardella . |
| 5,438,302 | 8/1995 | Goble . |
| 5,441,499 | 8/1995 | Fritzsch . |
| 5,443,470 | 8/1995 | Stern et al. . |
| 5,454,809 | 10/1995 | Janssen . |
| 5,462,521 | 10/1995 | Brucker et al. . |
| 5,472,441 | 12/1995 | Edwards et al. . |
| 5,472,443 | 12/1995 | Cordis et al. . |
| 5,480,397 | 1/1996 | Eggers et al. . |
| 5,480,398 | 1/1996 | Eggers et al. . |
| 5,496,312 | 3/1996 | Klicek . |
| 5,496,314 | 3/1996 | Eggers . |
| 5,505,728 | 4/1996 | Ellman et al. . |
| 5,505,730 | 4/1996 | Edwards . |
| 5,507,743 | 4/1996 | Edwards et al. . |
| 5,514,129 | 5/1996 | Smith . |
| 5,514,130 | 5/1996 | Baker . |
| 5,514,131 | 5/1996 | Edwards et al. . |
| 5,520,684 | 5/1996 | Imran . |
| 5,520,685 | 5/1996 | Wojciechowicz . |
| 5,522,815 | 6/1996 | Durgin, Jr. et al. . |
| 5,527,331 | 6/1996 | Kresch et al. . |
| 5,531,744 | 7/1996 | Nardella et al. . |
| 5,536,267 | 7/1996 | Edwards et al. . |
| 5,540,680 | 7/1996 | Guglielmi et al. . |
| 5,540,681 | 7/1996 | Strul et al. . |
| 5,540,682 | 7/1996 | Gardner et al. . |
| 5,540,683 | 7/1996 | Ichikawa et al. . |
| 5,540,684 | 7/1996 | Hassler, Jr. . |
| 5,540,685 | 7/1996 | Parins et al. . |
| 5,542,916 | 8/1996 | Hirsch et al. . |
| 5,542,945 | 8/1996 | Fritzsch . |
| 5,545,161 | 8/1996 | Imran . |
| 5,545,193 | 8/1996 | Fleischman et al. . |
| 5,549,605 | 8/1996 | Hahnen . |
| 5,554,172 | 9/1996 | Horner et al. . |
| 5,555,618 | 9/1996 | Winkler . |
| 5,556,396 | 9/1996 | Cohen et al. . |
| 5,556,397 | 9/1996 | Long et al. . |
| 5,558,671 | 9/1996 | Yates . |
| 5,562,720 | 10/1996 | Stern et al. . |
| 5,569,164 | 10/1996 | Lurz . |
| 5,569,242 | 10/1996 | Lax et al. . |
| 5,569,244 | 10/1996 | Hahnen . |
| 5,569,245 | 10/1996 | Guglielmi et al. . |
| 5,575,789 | 11/1996 | Bell et al. . |
| 5,578,007 | 11/1996 | Imran . |
| 5,582,609 | 12/1996 | Swanson et al. . |
| 5,582,610 | 12/1996 | Grossi et al. . |
| 5,584,830 | 12/1996 | Ladd et al. . |
| 5,591,141 | 1/1997 | Nettekoven . |
| 5,599,344 | 2/1997 | Paterson . |
| 5,599,345 | 2/1997 | Edwards et al. . |
| 5,599,346 | 2/1997 | Edwards et al. . |
| 5,599,347 | 2/1997 | Hart et al. . |
| 5,599,348 | 2/1997 | Gentelia et al. . |
| 5,599,349 | 2/1997 | D'Amelio . |
| 5,603,711 | 2/1997 | Parins et al. . |
| 5,603,712 | 2/1997 | Koranda et al. . |

| | | | | | | |
|---|---|---|---|---|---|---|
| 5,607,422 | 3/1997 | Smeets et al. . | | 19514552 | 10/1996 | (DE) . |
| 5,609,151 | 3/1997 | Mulier et al. . | | 19514553 C1 | 10/1996 | (DE) . |
| 5,609,573 | 3/1997 | Sandock . | | 0 013605 | 7/1980 | (EP) . |
| 5,611,798 | 3/1997 | Eggers . | | 0 049633 | 4/1982 | (EP) . |
| 5,620,481 | 4/1997 | Desai et al. . | | 0 067680 | 12/1982 | (EP) . |
| 5,624,439 | 4/1997 | Edwards et al. . | | 0 136855 | 4/1985 | (EP) . |
| 5,626,560 | 5/1997 | Soring . | | 0 219568 | 12/1985 | (EP) . |
| 5,626,575 | 5/1997 | Crenner . | | 0 205851 | 12/1986 | (EP) . |
| 5,626,576 | 5/1997 | Janssen . | | 0 280798A | 9/1988 | (EP) . |
| 5,626,578 | 5/1997 | Tihon . | | 0 310431 | 4/1989 | (EP) . |
| 5,628,745 | 5/1997 | Bek . | | 0316469 | 5/1989 | (EP) . |
| 5,628,771 | 5/1997 | Mizukawa et al. . | | 0 325456 | 7/1989 | (EP) . |
| 5,630,426 | 5/1997 | Eggers et al. . | | 0 332308 | 9/1989 | (EP) . |
| 5,633,578 | 5/1997 | Eggers et al. . | | 0 373670 | 6/1990 | (EP) . |
| 5,634,924 | 6/1997 | Turkel et al. . | | 0 392837 | 10/1990 | (EP) . |
| 5,672,174 | 9/1997 | Gough et al. . | | 0 407057 | 1/1991 | (EP) . |
| 5,683,366 | 11/1997 | Eggers et al. . | | 0 412426 | 2/1991 | (EP) . |
| 5,693,045 | 12/1997 | Eggers . | | 0 437377 | 7/1991 | (EP) . |
| 5,697,281 | 12/1997 | Eggers et al. . | | 0 448798 | 10/1991 | (EP) . |
| 5,697,536 | 12/1997 | Eggers et al. . | | 0 499491 | 8/1992 | (EP) . |
| 5,697,882 | 12/1997 | Eggers et al. . | | 0 507622 | 10/1992 | (EP) . |
| 5,697,909 | 12/1997 | Eggers et al. . | | 0 509670 | 10/1992 | (EP) . |
| 5,700,262 | 12/1997 | Acosta et al. . | | 0 517243 | 12/1992 | (EP) . |
| 5,725,524 | 3/1998 | Mulier et al. . | | 0 518230 | 12/1992 | (EP) . |
| 5,735,846 | 4/1998 | Panescu et al. . | | 0 530400 | 3/1993 | (EP) . |
| 5,766,153 | 6/1998 | Eggers et al. . | | 0 536440 | 4/1993 | (EP) . |
| 5,810,764 | 9/1998 | Eggers et al. . | | 0 558316 | 9/1993 | (EP) . |
| 5,830,214 | 11/1998 | Flom et al. . | | 0 558318 | 9/1993 | (EP) . |
| 5,833,689 | 11/1998 | Long . | | 0 647435 | 4/1995 | (EP) . |
| 5,843,019 | 12/1998 | Eggers et al. . | | 0 653192 | 5/1995 | (EP) . |
| 5,860,951 | 1/1999 | Eggers et al. . | | 0 674909 | 10/1995 | (EP) . |
| 5,871,469 | 2/1999 | Eggers et al. . | | 0 684015 | 11/1995 | (EP) . |
| 5,873,855 | 2/1999 | Eggers et al. . | | 0 688536 | 12/1995 | (EP) . |
| 5,888,198 | 3/1999 | Eggers et al. . | | 0 692224 | 1/1996 | (EP) . |
| 5,891,095 | 4/1999 | Eggers et al. . | | 0 694290 | 1/1996 | (EP) . |
| 5,902,272 | 5/1999 | Eggers et al. . | | 0 697199 | 2/1996 | (EP) . |
| 5,941,876 | 8/1999 | Nardella et al. . | | 0 709065 | 5/1996 | (EP) . |
| | | | | 0 714635 | 6/1996 | (EP) . |
| | | | | 0 717967 | 6/1996 | (EP) . |

FOREIGN PATENT DOCUMENTS

| | | | | | | |
|---|---|---|---|---|---|---|
| | | | | 0 732080 | 9/1996 | (EP) . |
| 2457900 | 5/1976 | (DE) . | | 0 733345 | 9/1996 | (EP) . |
| 2930982 | 2/1981 | (DE) . | | 0 737447 | 10/1996 | (EP) . |
| 3209444 | 10/1982 | (DE) . | | 57862 | 9/1953 | (FR) . |
| 3215832A | 11/1982 | (DE) . | | 1215305 | 4/1960 | (FR) . |
| 3119735 | 1/1983 | (DE) . | | 1454773 | 10/1966 | (FR) . |
| 3245570 | 6/1984 | (DE) . | | 2313949 | 1/1977 | (FR) . |
| 222207 | 5/1985 | (DE) . | | 2443829 | 7/1980 | (FR) . |
| 3423356 | 1/1986 | (DE) . | | 2501034 | 9/1982 | (FR) . |
| 3427517 | 1/1986 | (DE) . | | 2645008 | 10/1990 | (FR) . |
| 3511107 | 10/1986 | (DE) . | | 1361497 | 7/1974 | (GB) . |
| 3623688 | 1/1987 | (DE) . | | 2037167 | 7/1980 | (GB) . |
| 3530335 | 3/1987 | (DE) . | | 1583397 | 1/1981 | (GB) . |
| 3707820 | 9/1987 | (DE) . | | 2084880 | 4/1982 | (GB) . |
| 3622337 C2 | 1/1988 | (DE) . | | 2101893 | 1/1983 | (GB) . |
| 3642077 C2 | 6/1988 | (DE) . | | 2133290 | 7/1984 | (GB) . |
| 3708801 C2 | 9/1988 | (DE) . | | 2145932 | 4/1985 | (GB) . |
| 3824913 | 2/1990 | (DE) . | | 2161081 | 1/1986 | (GB) . |
| 3838840 C2 | 5/1990 | (DE) . | | 2164473 | 3/1986 | (GB) . |
| 3930451 | 3/1991 | (DE) . | | 2165761 | 4/1986 | (GB) . |
| 4108269 C2 | 6/1992 | (DE) . | | 2177309 | 1/1987 | (GB) |
| 4103972 C2 | 8/1992 | (DE) . | | 2179861 | 3/1987 | (GB) . |
| 4126608 | 2/1993 | (DE) . | | 2213381 | 8/1989 | (GB) . |
| 4139029 C2 | 6/1993 | (DE) . | | 2214430 | 9/1989 | (GB) . |
| 4217999 A1 | 12/1993 | (DE) . | | 2269538 | 2/1994 | (GB) . |
| 4237321 A1 | 5/1994 | (DE) . | | 62-211060 | 9/1987 | (JP) . |
| 4323585 | 1/1995 | (DE) . | | 644491 | 1/1979 | (RU) . |
| 4339049 | 5/1995 | (DE) . | | WO 81/03271 | 11/1981 | (WO) . |
| 4425015 | 1/1996 | (DE) . | | WO 82/00084 | 1/1982 | (WO) . |
| 19530004 | 3/1996 | (DE) . | | WO 82/02488 | 8/1982 | (WO) . |
| 4429478 | 3/1996 | (DE) . | | WO 84/03829 | 10/1984 | (WO) . |
| 19510185 | 10/1996 | (DE) . | | WO 88/01851 | 3/1988 | (WO) . |
| 19512640 C2 | 10/1996 | (DE) . | | | | |

| | | |
|---|---|---|
| WO 90/03152 | 4/1990 | (WO) . |
| WO 93/08756 | 5/1993 | (WO) . |
| WO 93/13718 | 7/1993 | (WO) . |
| WO 93/13816 | 7/1993 | (WO) . |
| WO 93/16650 | 9/1993 | (WO) . |
| WO 93/19681 | 10/1993 | (WO) . |
| WO 93/19682 | 10/1993 | (WO) . |
| WO 93/20747 | 10/1993 | (WO) . |
| WO 93/20877 | 10/1993 | (WO) . |
| WO 94/04220 | 3/1994 | (WO) . |
| WO 94/06510 | 3/1994 | (WO) . |
| WO 94/10921 | 5/1994 | (WO) . |
| WO 94/10924 | 5/1994 | (WO) . |
| WO 94/10925 | 5/1994 | (WO) . |
| WO 94/23659 | 10/1994 | (WO) . |
| WO 94/26228 * | 11/1994 | (WO) . |
| WO 94/28809 | 12/1994 | (WO) . |
| WO 95/02369 | 1/1995 | (WO) . |
| WO 95/05781 | 3/1995 | (WO) . |
| WO 95/09576 | 4/1995 | (WO) . |
| WO 95/09577 | 4/1995 | (WO) . |
| WO 95/10320 | 4/1995 | (WO) . |
| WO 95/10321 | 4/1995 | (WO) . |
| WO 95/17855 | 7/1995 | (WO) . |
| WO 95/18575 | 7/1995 | (WO) . |
| WO 95/19733 | 7/1995 | (WO) . |
| WO 95/20360 | 8/1995 | (WO) . |
| WO 95/23558 | 9/1995 | (WO) . |
| WO 95/24160 | 9/1995 | (WO) . |
| WO 95/25472 | 9/1995 | (WO) . |
| WO 95/26686 | 10/1995 | (WO) . |
| WO 95/30377 | 11/1995 | (WO) . |
| WO 95/31144 | 11/1995 | (WO) . |
| WO 96/00036 | 1/1996 | (WO) . |
| WO 96/00039 | 1/1996 | (WO) . |
| WO 96/00040 | 1/1996 | (WO) . |
| WO 96/00042 | 1/1996 | (WO) . |
| WO 96/00043 | 1/1996 | (WO) . |
| WO 96/00528 | 1/1996 | (WO) . |
| WO 96/04859 | 2/1996 | (WO) . |
| WO 96/07360 | 3/1996 | (WO) . |
| WO 96/09010 | 3/1996 | (WO) . |
| WO 96/10367 | 4/1996 | (WO) . |
| WO 96/11638 | 4/1996 | (WO) . |
| WO 96/14020 | 5/1996 | (WO) . |
| WO 96/14021 | 5/1996 | (WO) . |
| WO 96/18349 | 6/1996 | (WO) . |
| WO 96/19152 | 6/1996 | (WO) . |
| WO 96/23448 | 8/1996 | (WO) . |
| WO 96/23449 | 8/1996 | (WO) . |
| WO 96/24296 | 8/1996 | (WO) . |
| WO 96/24301 | 8/1996 | (WO) . |
| WO 96/27337 | 9/1996 | (WO) . |
| WO 96/29946 | 10/1996 | (WO) . |
| WO 96/32897 | 10/1996 | (WO) . |

OTHER PUBLICATIONS

Schurr, M. O. et al., "Histologic Effects of Different Technologies for Dissection in Endoscopic Surgery:Nd:YAG Laser, High Frequency and Water–Jet," End. Surg., vol. 2, 1994, pp. 195–201.

Newman, Laura, "Could Twist on TURP Knock Lasers Out," Urology Times, vol. 3, No. 3, Mar. 1995, p. 21.

AthroCare Corporation, "The Arthrocare Anthroscopic System," 1995.

Tucker, R.D. et al., "In Vivo Effect of 5 French Bipolar and Monopolar Electro–Surgical Probes on Porcine Bladder," Urological Research, Springer–Verlag 1990, 18:291–294.

Kramolowsky, Eugene V. et al., "The Urological Application of Electrosurgery," The Journal of Urology, vol. 146, Sep. 1991, pp. 669–674.

Tucker, Robert D. et al., "A Comparison of Urologic Application of Bipolar Versus Monopolar Five French Electrosurgical Probes," The Journal of Urology, vol. 141, Mar. 1989, pp. 662–665.

Kramolowsky, Eugene V. et al., "Use of 5F Bipolar Electrosurgical Probe in Endoscopic Urological Procedures," The Journal of Urology, vol. 143, Feb. 1990, pp. 275–277.

Tucker, Robert et al., A Bipolar Electrosurgical TURP Loop, Abstract of Paper P14–11, $7^{th}$ World Congress on Endourology and ESWL, Nov. 27–30, Kyoto, Japan, 1989, p. 248.

Ramsay, J.W. A. et al., "A Comparison of Bipolar and Monopolar Diathermy Probes in Experimental Animals," Urological Research, Springer–Verlag 1985, 13:99–102.

German Article w/Translation: Elsasser, E. and Roos, E., "Concerning an Instrument for Transurethral Resection without Leakage of Current," Medizinal–Marks/Acta Medicotechnica, vol. 24, No. 4, 1976, pp. 129–134.

Nardella, Paul C., "Radio Frequency Energy and Impedance Feedback," SPIE, vol. 1068, Catheter–Based Sensing & Imaging Technology, 1989, pp. 42–48.

Honig, William M., "The Mechanism of Cutting in Electrosurgery," IEEE Transactions on Biomedical Engineering, Jan. 1975, pp. 58–65.

Barry, Kevin J. et al., "The Effect of Radiofrequency–Generated Thermal Energy on the Mechanical and Histologic Characteristics of the Arterial Wall In Vivo: Implications for Radiofrequency Angioplasty," American Heart Journal, vol. 117, No. 2, Feb. 1989, pp. 332–341.

Slager, Cornelis J. et al., "Vaporization of Atherosclerotic Plaques by Spark Erosion," Journal of American College of Cardiology, 1985, pp. 1382–1386.

Lee, Benjamin I. et al., "Thermal Compression and Molding of Atherosclerotic Vascular Tissue with Use of Radiofrequency Energy: Implications for Radiofrequency Balloon Angioplasty," Journal of American College of Cardiology, vol. 13, No. 5, Apr. 1989, pp. 167–175.

Piercey, J.R.A. et al., "Electrosurgical Treatment of Experimental Bleeding Canine Gastric Ulcers," Gastroenterology, vol. 74, No. 3, 1978, pp. 527–534.

Protell, Robert L. et al., "Computer–Assisted Electrocoagulation: Bipolar vs. Monopolar in the Treatment of Experimental Canine Gastric Ulcer Bleeding," Gastroenterology, vol. 80, No. 3, 1981, pp. 451–455.

Johnston, James H. et al., "Experimental Comparison of Endoscopic Yttrium–Aluminum–Garnet Laser, Electrosurgery, and Heater Probe for Canine Gut Arterial Coagulation," Gastroenterology, vol. 92, No. 5, May 1987, pp. 1101–1108.

Dennis, M.B. et al., "Evaluation of Electrofulguration in Control of Bleeding of Experimental Gastric Ulcers," Digestive Diseases and Sciences, vol. 24, No. 11, Nov. 1979, pp. 845–848.

Silverstein, Fred E. et al., "Endoscopic Hemostasis Using Laser Photocoagulation and Electrocoagulation," Digestive Diseases and Sciences, vol. 26, No. 7, Jul. Supplement 1981, pp. 31s–40s.

Auth, D.C., "Animal Testing of Endoscopic Hemostasis with Lasers and Other Devices," Endoscopy, vol. 18, Supplement 2, May 1986, pp. 36–39.

McLean, A.J., "The Bovie Electrosurgical Current Generator—Some Underlying Principles and Results," Archives of Surgery, vol. 18, 1929, pp. 1863–1873.

McLean, A.J., "Characteristics of Adequate Electrosurgical Current," American Journal of Surgery, vol. XVIII, No. 3, Feb. 16, 1932, pp. 417–441.

Wattiez, Arnaud et al., *Electrosurgery in Operative Endoscopy*, Blackwell Science Ltd., London, 1995, pp. 87–93, 155–163.

Farin, G., "Pneumatically Controlled Bipolar Cutting Instrument," End. Surg., 1993, pp. 1–3.

Muller, W., "The Advantages of Laparoscopic Assisted Bipolar High–Frequency Surgery," End. Surg., 1993, pp. 1–6.

Reidenbach, H. D., "Fundamentals of Bipolar High–Frequency Surgery," End. Surg. 1993, pp. 85–90.

Penketh, Richard et al., "Clinical Evaluation of the Procision Bipolar Electrosurgical Generator During Laparoscopic Gynaecological Procedures," EAES, $2^{nd}$ International Congress of the European Association for Endoscopic Surgery, Madrid, Sep. 15–17, 1994.

Lloyd, David M. et al., "A New Portable Bipolar Generator–Use in Laparoscopic Cholecystectomy," EAES, $2^{nd}$ International Congress of the European Association for Endoscopic Surgery, Madrid, Sep. 15–17, 1994.

Buchelt, Martin et al., "Excimer Laser Ablation of Fibrocartilage: An In Vitro and In Vivo Study," Lasers in Surgery and Medicine, vol. 11, 1991, pp. 271–279.

Srinivasan, R., "Ablation of Polymers and Biological Tissue by Ultraviolet Lasers," Science, vol. 234, Oct. 31, 1986, pp. 559–565.

Pearce, John A., "Chapter 3 Electrosurgery," *Handbook of Biomedical Engineering*, Ed. Jacob Kline, Academic Press, Inc., 1988, pp. 99–113.

Selikowitz, Stuart M. et al., "Electric Current and Voltage Recordings on the Myocardium During Electrosurgical Procedures in Canines," *Reprint from Surgery, Gynecology & Obstetrics*, Mar. 1987, vol. 164, pp. 219–224.

Tucker, Robert D. et al., "Demodulated Low Frequency Currents from Electrosurgical Procedures," Surgery, Gynecology & Obstetrics, Jul. 1984, vol. 159, pp. 39–43.

Lu, David Y. et al., "Electrical Thermal Angioplasty: Catheter Design Features, In Vitro Tissue Ablation Studies and In Vivo Experimental Findings," Am J Cardiol, vol. 60, 1987, pp. 1117–1122.

Malis, Leonard I., "Electrosurgery: Technical Note," J. Neurosurg., vol. 85, 1996, pp. 970–975.

Slager, C. J. et al., "Spark Erosion of Arteriosclerotic Plaques," Kardiologie, vol. 76, Suppl. 6, 1987, pp. 67–71.

Geddes, Leslie A., *Medical Device Accidents—With Illustrative Cases*, CRC Press, New York, 1998, p. 93 (commentary on Honig, William M., "The Mechanism of Cutting in Electrosurgery," IEEE Transactions on Biomedical Engineering Jan. 1975, pp. 58–65).

Valleylab, Inc., "Force Electrosurgical Generators Instruction Manual," Valleylab Part No. 945 110 039 A, Feb. 1987, pp. 59–62.

Valleylab, Inc., "Advances in Bipolar Electrosurgery for Laparoscopic Surgery," Advances in Bipolar Electrosurgery, pp. 1–4.

Description of Codman and Johnson & Johnson Malis CMC–III Bipolar System.

Pfizer/Valleylab Press Release "Valleylab Inc. Introduces The Procision Bipolar Electrosurgery System," Sep. 15, 1994.

ArthroCare Corporation, "ArthroCare Arthroscopic Electrosurgery System, Model 970 Operator's Manual," Feb. 1996.

* cited by examiner

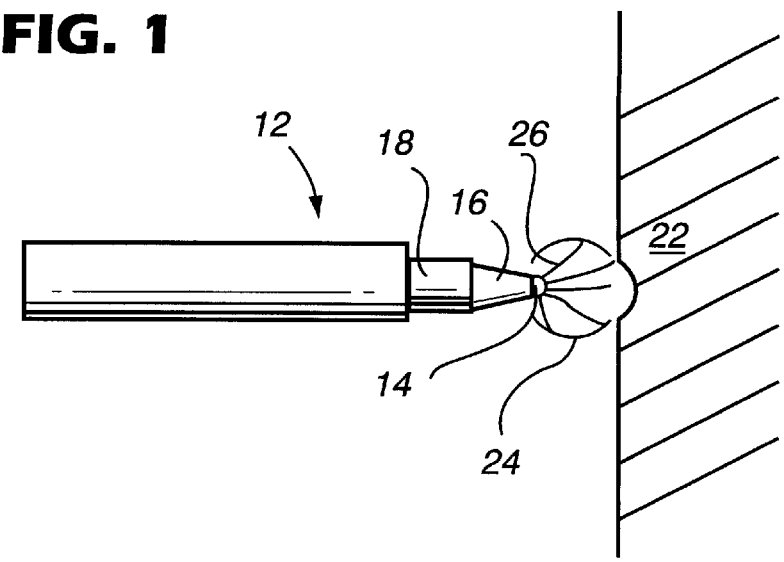
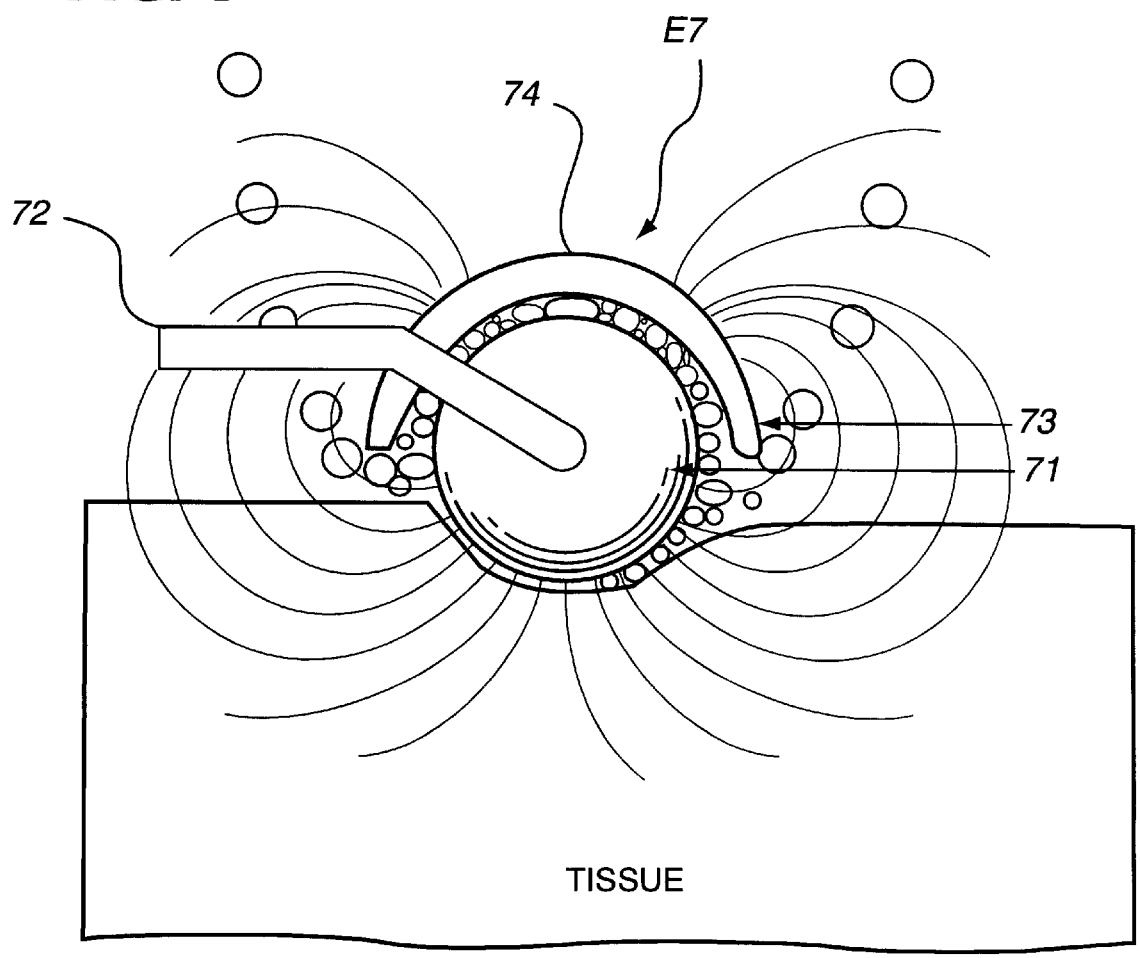

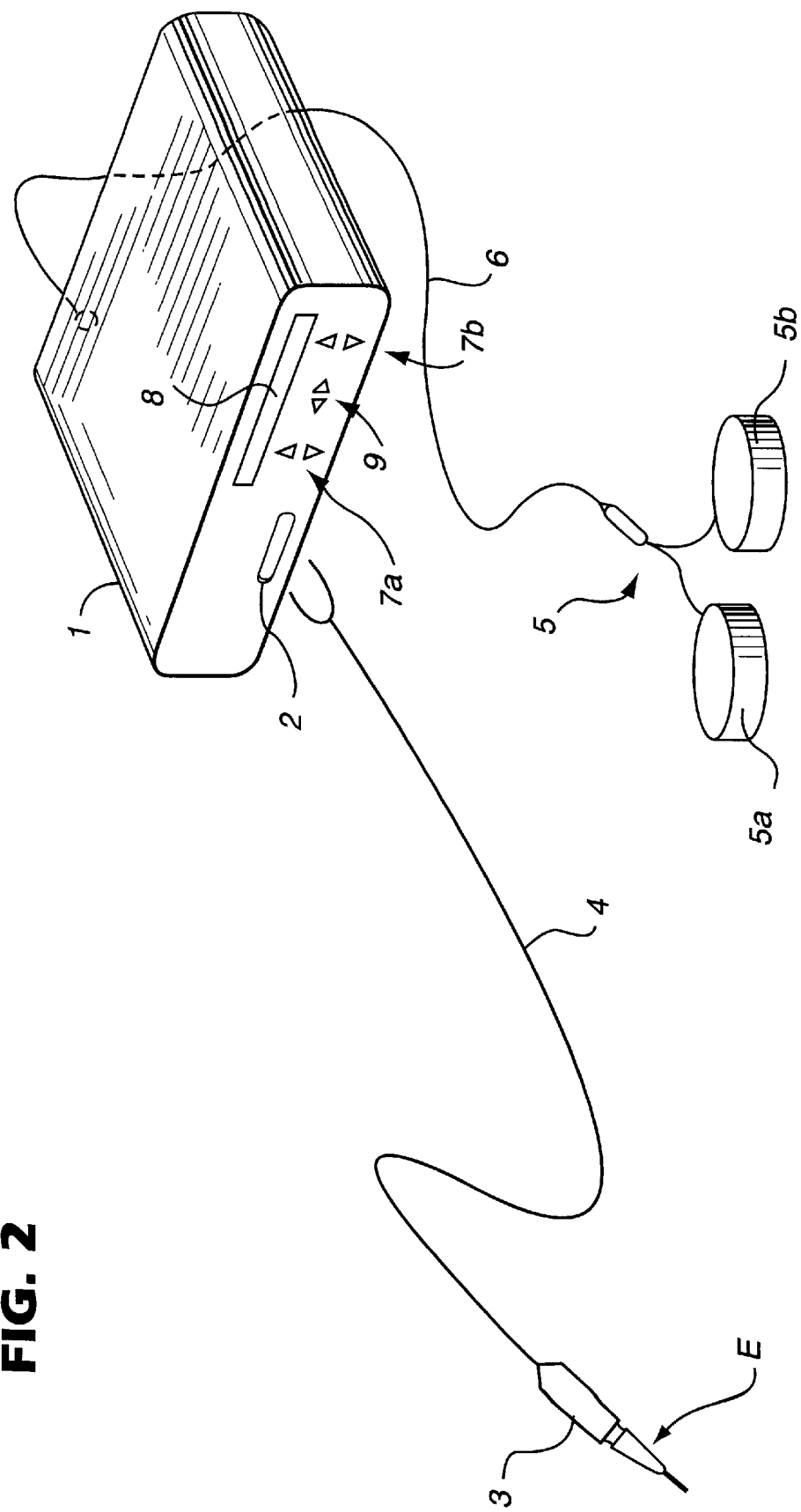

ELECTROSURGICAL INSTRUMENT

This is a divisional of application Ser. No. 08/740,258, filed Oct. 25, 1996, now U.S. Pat. No. 6,013,076.

BACKGROUND OF THE INVENTION

This invention relates to an electrosurgical instrument for the treatment of tissue in the presence of an electrically conductive fluid medium, to electrosurgical apparatus including such an instrument, and to an electrode unit for use in such an instrument.

Endoscopic electrosurgery is useful for treating tissue in cavities of the body, and is normally performed in the presence of a distension medium. When the distension medium is a liquid, this is commonly referred to as underwater electrosurgery, this term denoting electrosurgery in which living tissue is treated using an electrosurgical instrument with a treatment electrode or electrodes immersed in liquid at the operation site. A gaseous medium is commonly employed when endoscopic surgery is performed in a distensible body cavity of larger potential volume in which a liquid medium would be unsuitable, as is often the case in laparoscopic or gastroenterological surgery.

Underwater surgery is commonly performed using endoscopic techniques, in which the endoscope itself may provide a conduit (commonly referred to as a working channel) for the passage of an electrode. Alternatively, the endoscope may be specifically adapted (as a resectoscope) to include means for mounting an electrode, or the electrode may be introduced into a body cavity via a separate access means at an angle with respect to the endoscope—a technique commonly referred to as triangulation. These variations in technique can be subdivided by surgical speciality, where one or other of the techniques has particular advantages given the access route to the specific body cavity. Endoscopes with integral working channels, or those characterised as resectoscopes, are generally employed when the body cavity may be accessed through a natural body opening - such as the cervical canal to access the endometrial cavity of the uterus, or the urethra to access the prostate gland and the bladder. Endoscopes specifically designed for use in the endometrial cavity are referred to as hysterocopes, and those designed for use in the urinary tract include cystoscopes, urethroscopes and resectoscopes. The procedures of transurethal resection or vaporisation of the prostate gland are known as TURP and EVAP respectively. When there is no natural body opening through which an endoscope may be passed, the technique of triangulation is commonly employed. Triangulation is commonly used during underwater endoscopic surgery on joint cavities such as the knee and the shoulder. The endoscope used in these procedures is commonly referred to an as arthroscope.

Electrosurgery is usually carried out using either a monopolar instrument or a bipolar instrument. With monopolar electrosurgery, an active electrode is used in the operating region, and a conductive return plate is secured to the patient's skin. With this arrangement, current passes from the active electrode through the patient's tissues to the external return plate. Since the patient represents a significant portion of the circuit, input power levels have to be high (typically 150 to 250 watts), to compensate for the resistive current limiting of the patient's tissues and, in the case of underwater electrosurgery, power losses due to the fluid medium which is rendered partially conductive by the presence of blood or other body fluids. Using high power with a monopolar arrangement is also hazardous, due to the tissue heating that occurs at the return plate, which can cause severe skin burns. There is also the risk of capacitive coupling between the instrument and patient tissues at the entry point into the body cavity.

With bipolar electrosurgery, a pair of electrodes (an active electrode and a return electrode) are used together at the tissue application site. This arrangement has advantages from the safety standpoint, due to the relative proximity of the two electrodes so that radio frequency currents are limited to the region between the electrodes. However, the depth of effect is directly related to the distance between the two electrodes; and, in applications requiring very small electrodes, the inter-electrode spacing becomes very small, thereby limiting tissue effect and the output power. Spacing the electrodes further apart would often obscure vision of the application site, and would require a modification in surgical technique to ensure correct contact of both electrodes with the tissue.

There are a number of variations to the basic design of the bipolar probe. For example, U.S. Pat. No. 4,706,667 describes one of the fundamentals of the design, namely that the ratio of the contact areas of the return electrode and of the active electrode is greater than 7:1 and smaller than 20:1 for cutting purposes. This range relates only to cutting electrode configurations. When a bipolar instrument is used for desiccation or coagulation, the ratio of the contact areas of the two electrodes may be reduced to approximately 1:1 to avoid differential electrical stresses occurring at the contact between the tissue and the electrodes.

The electrical junction between the return electrode and tissue can be supported by wetting of the tissue by a conductive solution such as normal saline. This ensures that the surgical effect is limited to the needle or active electrode, with the electric circuit between the two electrodes being completed by the tissue. One of the obvious limitations with the design is that the needle must be completely buried in the tissue to enable the return electrode to complete the circuit. Another problem is one of the orientation: even a relatively small change in application angle from the ideal perpendicular contact with respect to the tissue surface, will change the contact area ratio, so that a surgical effect can occur in the tissue in contact with the return electrode.

Cavity distension provides space for gaining access to the operation site, to improve visualisation, and to allow for manipulation of instruments. In low volume body cavities, particularly where it is desirable to distend the cavity under higher pressure, liquid rather than gas is more commonly used due to better optical characteristics, and because it washes blood away from the operative site.

Conventional underwater electrosurgery has been performed using a non-conductive liquid (such as 1.5% glycine) as an irrigant, or as a distension medium to eliminate electrical conduction losses. Glycine is used in isotonic concentrations to prevent osmotic changes in the blood when intra-vascular absorption occurs. In the course of an operation, veins may be severed, with resultant infusion of the liquid into the circulation, which could cause, among other things, a dilution of serum sodium which can lead to a condition known as water intoxication.

The applicants have found that it is possible to use a conductive liquid medium, such as normal saline, in underwater endoscopic electrosurgery in place of non-conductive, electrolyte-free solutions. Normal saline is the preferred distension medium in underwater endoscopic surgery when electrosurgery is not contemplated, or a non-electrical tissue effect such as laser treatment is being used. Although normal saline (0.9% w/v; 150 mmol/l) has an electrical conductivity somewhat greater than that of most body tissue, it has the advantage that displacement by absorption or extravasation from the operative site produces little physiological effect, and the so-called water intoxication effects of non-conductive, electrolyte-free solutions are avoided.

The applicants have developed a bipolar instrument suitable for underwater electrosurgery using a conductive liquid or gaseous medium. This electrosurgical instrument for the treatment of tissue in the presence of a fluid medium, comprises an instrument body having a handpiece and an instrument shaft and an electrode assembly, at one end of the shaft. The electrode assembly comprises a tissue treatment electrode which is exposed at the extreme distal end of the instrument, and a return electrode which is electrically insulated from the tissue treatment electrode and has a fluid contact surface spaced proximally from the exposed part of the tissue treatment electrode. In use of the instrument, the tissue treatment electrode is applied to the tissue to be treated whilst the return electrode, being spaced proximally from the exposed part of the tissue treatment electrode, is normally spaced from the tissue and serves to complete an electrosurgical current loop from the tissue treatment electrode through the tissue and the fluid medium. This electrosurgical instrument is described in the specification of the applicants' co-pending International Patent Application No. PCT/GB96/01473, the contents of which are incorporated in this application by reference.

The electrode structure of this instrument, in combination with an electrically conductive fluid medium largely avoids the problems experienced with monopolar or bipolar electrosurgery. In particular, input power levels are much lower than those generally necessary with a monopolar arrangement (typically 100 watts). Moreover, because of the relatively large spacing between its electrodes, an improved depth of effect is obtained compared with a conventional bipolar arrangement.

FIG. 1 illustrates the use of this type of instrument for tissue removal by vaporisation. The electrode assembly 12 of this instrument comprises a tissue treatment (active) electrode 14 which is exposed at the distal end of the instrument, and a return electrode which is spaced from the exposed part of the tissue treatment electrode by an insulation sleeve 16. This electrode assembly is powered to create a sufficiently high energy density at the tissue treatment electrode 14 to vaporise tissue 22, and to create a vapour pocket 24 surrounding the active tip. The formation of the vapour pocket 24 creates about a 10-fold increase in contact impedance, with a consequent increase in output voltage. Arcs 26 are created in the vapour pocket 24 to complete the circuit to the return electrode 18. Tissue 22 which contacts the vapour pocket 24 will represent a path of least electrical resistance to complete the circuit. The closer the tissue 22 comes to the electrode 14 the more energy is concentrated to the tissue, to the extent that the cells explode as they are struck by the arcs 26, because the return path through the conductive fluid (saline in this case) is blocked by the high impedance barrier of the vapour pocket 24. The saline solution also acts to dissolve the solid products of vaporisation.

The power threshold required to reach vaporisation is an important parameter of this type of instrument, and it is the aim of the invention to provide a bipolar electrosurgical instrument having improved vaporisation power threshold properties.

SUMMARY OF THE INVENTION

In its broadest aspect, the invention provides an electrosurgical instrument having an electrode which is so constructed as to have a better vaporisation power threshold than known electrodes.

Thus, according to a first aspect, the present invention provides an electrosurgical instrument for the treatment of tissue in the presence of an electrically-conductive fluid, the instrument comprising an instrument shaft, and a tissue treatment electrode at one end of the shaft, the tissue treatment electrode being constructed to define a plurality of pockets for trapping electrically-conductive fluid and vapour.

In use, the tissue treatment electrode traps electrically-conductive fluid, the trapped fluid thereby absorbing more electrical power for conversion to vapour than would otherwise be the case. This leads to a reduction in the power threshold for vaporisation at the tissue treatment electrode.

The electrically conductive fluid trapped within the irregularities (pockets) of the tissue treatment electrode progressively absorbs more power as it becomes hotter and is not refreshed by fluid from the surrounding environment. As the fluid approaches boiling point, vapour pockets begin to form on the surface of the electrode. The vapour pockets effectively insulate regions of the electrode from the conductive fluid; and, as a result, power becomes concentrated at regions of the electrode not enveloped in vapour. Fluid adjacent to these exposed regions then rapidly reaches a point of vaporisation such that the whole tissue treatment electrode becomes coated in vapour. The vapour is entrapped by the irregular form of the active electrode such that, if an area of the electrode becomes exposed to the fluid medium during use, then the vapour pocket is rapidly reestablished with minimal power dissipation to the surrounding fluid. This leads to a reduction in the power threshold required both to initiate and sustain the vapour pocket during use.

In a preferred embodiment, the tissue treatment electrode is constituted by a plurality of interlaced strands of electrically-conductive material. In this case, the pockets are defined by the interlacing of the strands. Each strand may be formed as a helix, the helices preferably having a common central axis, and being of equal diameter and equal pitch. They may be so interlaced that the pockets formed between them take the form of helical apertures providing fluid communication between an axially-extending space within the helices and the space outside the helices. In another variant, the helices may be tightly wound together, so that each helix lies against other helices and the above-mentioned pockets are simply helical recesses between neighbouring helices, little or no communication being available between an interior space and the outside of the electrode. It is possible to achieve a similar function to the tightly-wound, interlaced strand variant with a single piece of conductive material with helical ridges about its outer surface, either created by moulding, machining, or by twisting the piece of material about its longitudinal axis, with the twisting causing helical ridges about the outer surface of the material.

Alternatively, the tissue treatment electrode is constituted by a generally helical coil made of electrically-conductive material. Here, the pockets are formed between adjacent turns of the helical coil. Again, the turns of the coil may be spaced apart to allow communication between the interior of the coil and the outside, or they may be tightly abutting with the pockets comprising a single helical recess on the outer surface of the electrode.

The tissue treatment electrode may also be constituted by a plurality of filaments made of an electrically-conductive material. In this case, the spaces between the filaments define the pockets.

In any of these cases, the instrument may further comprise an insulating shroud which extends along, and partially surrounds, the tissue treatment electrode. The shroud traps electrically-conductive fluid and vapour against the tissue treatment electrode, thereby enhancing its power absorption capabilities.

In another preferred embodiment, the tissue treatment electrode is constituted by a spherical member made of electrically-conductive material, the spherical member being mounted on the shaft of the instrument by means of an electrically-conductive support member, the instrument further comprising an insulating shroud which partially surrounds the spherical member.

Advantageously, the tissue treatment electrode is made of tungsten, a noble metal such as platinum, or of a platinum alloy such as platinum/iridium, platinum/tungsten or platinum/cobalt.

Preferably, the instrument further comprises a return electrode which is electrically insulated from the tissue treatment electrode by means of an insulation member, the tissue treatment electrode being exposed at the extreme distal end of the instrument, and the return electrode having a fluid contact surface spaced proximally from the exposed end of the tissue treatment electrode by the insulation member. Conveniently, the fluid contact surface of the return electrode is a smooth polished surface.

According to a second aspect, the present invention provides an electrosurgical instrument for the treatment of tissue in the presence of an electrically-conductive fluid, the instrument comprising an instrument shaft, and a tissue treatment electrode at one end of the shaft, the tissue treatment electrode being made from an electrically-conductive material and being coated with a resistive inert material which is effective to increase the local power density within the tissue treatment electrode.

Preferably, the resistive inert material is constituted by a conductive ceramic material.

According to a third aspect, the present mention provides an electrosurgical instrument for the treatment of tissue in the presence of an electrically-conductive fluid, the instrument comprising an instrument shaft, and an electrode assembly at one end of the shaft, the electrode assembly comprising a tissue treatment electrode and a return electrode which is electrically insulated from the tissue treatment electrode by means of an insulation member, the tissue treatment electrode being exposed at the extreme distal end of the instrument, and the return electrode having a smooth, polished, fluid contact surface spaced proximally from the exposed end of the tissue treatment electrode by the insulation member.

In this case the instrument may further comprise means for feeding electrically-conductive fluid over the fluid contact surface of the return electrode.

The electrosurgical instrument of the invention is useful for dissection, resection, vaporisation, desiccation and coagulation of tissue and combinations of these functions with particular application in hysteroscopic surgical procedures. Hysteroscopic operative procedures may include: removal of submucosal fibroids, polyps and malignant neoplasms; resection of congenital uterine anomalys such as a septum or subseptum; division of synechiae (adhesiolysis); ablation of diseased or hypertrophic endometrial tissue; and haemostasis.

The instrument of the invention is also useful for dissection, resection, vaporisation, desiccation and coagulation of tissue and combinations of these functions with particular application in arthroscopic surgery as it pertains to endoscopic and percutaneous procedures performed on joints of the body including, but not limited to, such techniques as they apply to the spine and other non-synovial joints. Arthroscopic operative procedures may include: partial or complete meniscectomy of the knee joint including meniscal cystectomy; lateral retinacular release of the knee joint; removal of anterior and posterior cruciate ligaments or remnants thereof; labral tear resection, acromioplasty, bursectomy and subacromial decompression of the shoulder joint; anterior release of the temperomandibular joint; synovectomy, cartilage debridement, chondroplasty, division of intra-articular adhesions, fracture and tendon debridement as applied to any of the synovial joints of the body; inducing thermal shrinkage of joint capsules as a treatment for recurrent dislocation, subluxation or repetitive stress injury to any articulated joint of the body; discectomy either in the treatment of disc prolapse or as part of a spinal fusion via a posterior or anterior approach to the cervical, thoracic and lumbar spine or any other fibrous joint for similar purposes; excision of diseased tissue; and haemostasis.

The instrument of the invention is also useful for dissection, resection, vaporisation, desiccation and coagulation of tissue and combinations of these functions with particular application in urological endoscopic (urethroscopy, cystoscopy, ureteroscopy and nephroscopy) and percutaneous surgery. Urological procedures may include: electro-vaporisation of the prostrate gland (EVAP) and other variants of the procedure commonly referred to as transurethral resection of the prostate (TURP) including, but not limited to, interstitial ablation of the prostate gland by a percutaneous or perurethral route whether performed for benign or malignant disease; transurethral or percutaneous resection of urinary tract tumours as they may arise as primary or secondary neoplasms, and further as they may arise anywhere in the urological tract from the calyces of the kidney to the external urethral meatus; division of strictures as they may arise at the pelviureteric junction (PUJ), ureter, ureteral orifice, bladder neck or urethra; correction of ureterocoele shrinkage of bladder diverticular, cystoplasty procedures as they pertain to corrections of voiding dysfunction; thermally induced shrinkage of the pelvic floor as a corrective treatment for bladder neck descent; excision of diseased tissue; and haemostasis.

Surgical procedures using the instrument of the invention include introducing the electrode assembly to the surgical site whether through an artificial conduit (a cannula), or through a natural conduit which may be in an anatomical body cavity or space or one created surgically. The cavity or space may be distended during the procedure using a fluid, or may be naturally held open by anatomical structures. The surgical site may be bathed in a continuous flow of conductive fluid such as saline solution to fill and distend the cavity. The procedures may include simultaneous viewing of the site via an endoscope or using an indirect visualisation means.

The invention also provides an electrode unit for an electrosurgical instrument for the treatment of tissue in the presence of an electrically-conductive fluid medium, the electrode unit comprising a shaft having at one end means for connection to an instrument handpiece, and, mounted on the other end of the shaft, a tissue treatment electrode, the tissue treatment electrode being constructed to define pockets for trapping electrically-conductive fluid and vapour.

The invention further provides an electrode unit for an electrosurgical instrument for the treatment of tissue in the presence of an electrically-conductive fluid medium, the electrode unit comprising a shaft having at one end means for connection to an instrument handpiece, and, mounted on the other end of the shaft, a tissue treatment electrode, the tissue treatment electrode being made from an electrically-conductive material and being coated with a resistive inert material which is effective to increase the local power density within the tissue treatment electrode.

The invention still further provides electrosurgical apparatus comprising a radio frequency generator and an electrosurgical instrument for the treatment of tissue in the pressure of an electrically-conductive fluid medium, the instrument comprising an instrument shaft, and an electrode assembly at one end of the shaft, the electrode assembly comprising a tissue treatment electrode and a return electrode which is electrically insulated from the tissue treatment electrode by means of an insulation member, the tissue treatment electrode being exposed at the distal end portion of the instrument, the return electrode having a fluid contact surface spaced proximally from the exposed end of the tissue treatment electrode by the insulation member, and the radio frequency generator having a bipolar output connected to the electrodes, wherein the exposed end of the tissue treatment electrode is constructed to define a plurality of pockets for trapping electrically-conductive fluid and vapour.

The invention also provides electrosurgical apparatus comprising a radio frequency generator and an electrosurgical instrument for the treatment of tissue in the presence of an electrically-conductive fluid medium, the instrument comprising an instrument shaft, and an electrode assembly at one end of the shaft, the electrode assembly comprising a tissue treatment electrode and a return electrode which is electrically insulated from the tissue treatment electrode by means of an insulation member, the tissue treatment electrode being exposed at the distal end portion of the instrument, the return electrode having a fluid contact surface spaced proximally from the exposed end of the tissue treatment electrode by the insulation member, and the radio frequency generator having a bipolar output connected to the electrodes, wherein the exposed end of the tissue treatment electrode is made from an electrically-conductive material and is coated with a resistive inert material which is effective to increase the local power density within the tissue treatment electrode.

Advantageously, the radio frequency generator includes control means for varying the output power delivered to the electrodes. Preferably, the control means is such as to provide output power in first and second output ranges, the first output range being for powering the electrosurgical instrument for tissue desiccation, and the second output range being for powering the electrosurgical instrument for tissue removal by vaporisation. Conveniently, the first output range is from about 150 volts to 200 volts, and the second output range is from about 250 volts to 600 volts, the voltages being peak voltages.

The invention further provides a method of operating an electrosurgical apparatus having at least a tissue desiccation mode and a tissue vaporisation mode, the apparatus having a radio frequency generator coupled to an electrode assembly for the treatment of tissue in the presence of an electrically-conductive fluid medium, the electrode assembly comprising a tissue treatment electrode and a return electrode which is electrically insulated from the tissue treatment electrode by means of an insulation member, the tissue treatment electrode being exposed at the distal end portion of the assembly, and the return electrode having a fluid contact surface spaced proximally from the exposed end of the tissue electrode by the insulation member, the method comprising the steps of: controlling the output power of the radio frequency generator to lie within a first output range for the tissue desiccation mode and to lie within a second output range for the tissue vaporisation mode, the first output range being such that the power supplied to the electrode assembly maintains the conductive fluid adjacent to the tissue treatment electrode substantially at boiling point for tissue desiccation without creating a vapour pocket surrounding the tissue treatment electrode, and the second output range is such that the output power supplied to the electrode assembly for vaporisation of tissue is such as to maintain a vapour pocket surrounding the tissue treatment electrode; and reducing the power threshold for vaporisation at the tissue treatment electrode when the output power of the radio frequency generator is in the second output range.

The invention still further provides an electrosurgical method comprising the steps of: providing an electrosurgical apparatus comprising a radio frequency generator coupled to an electrode assembly comprising a tissue treatment electrode and a return electrode, the tissue treatment electrode being exposed at the distal end portion of the assembly; introducing the electrode assembly into a selected operation site with the tissue treatment electrode adjacent to the tissue to be treated, and with the tissue and the tissue electrode assembly immersed in a conductive liquid; activating the generator; applying sufficient radio frequency power to the electrode assembly to vaporise the conductive liquid surrounding the tissue treatment electrode to maintain a vapour pocket surrounding the tissue treatment electrode; and reducing the power threshold for vaporisation at the tissue treatment electrode.

BRIEF DESCRIPTION OF THE DRAWINGS

The invention will now be described in greater detail, by way of example, with reference to the drawings, in which:

FIG. 1 is a diagrammatic side elevation of an electrode unit, showing the use of such a unit for tissue removal by vaporisation;

FIG. 2 is a diagram showing an electrosurgical apparatus constructed in accordance with the invention;

FIG. 9 is a diagrammatic side elevation of the electrode assembly of a sixth form of electrode unit constructed in accordance with the invention;

DETAILED DESCRIPTION OF THE DRAWINGS

Figure 3:
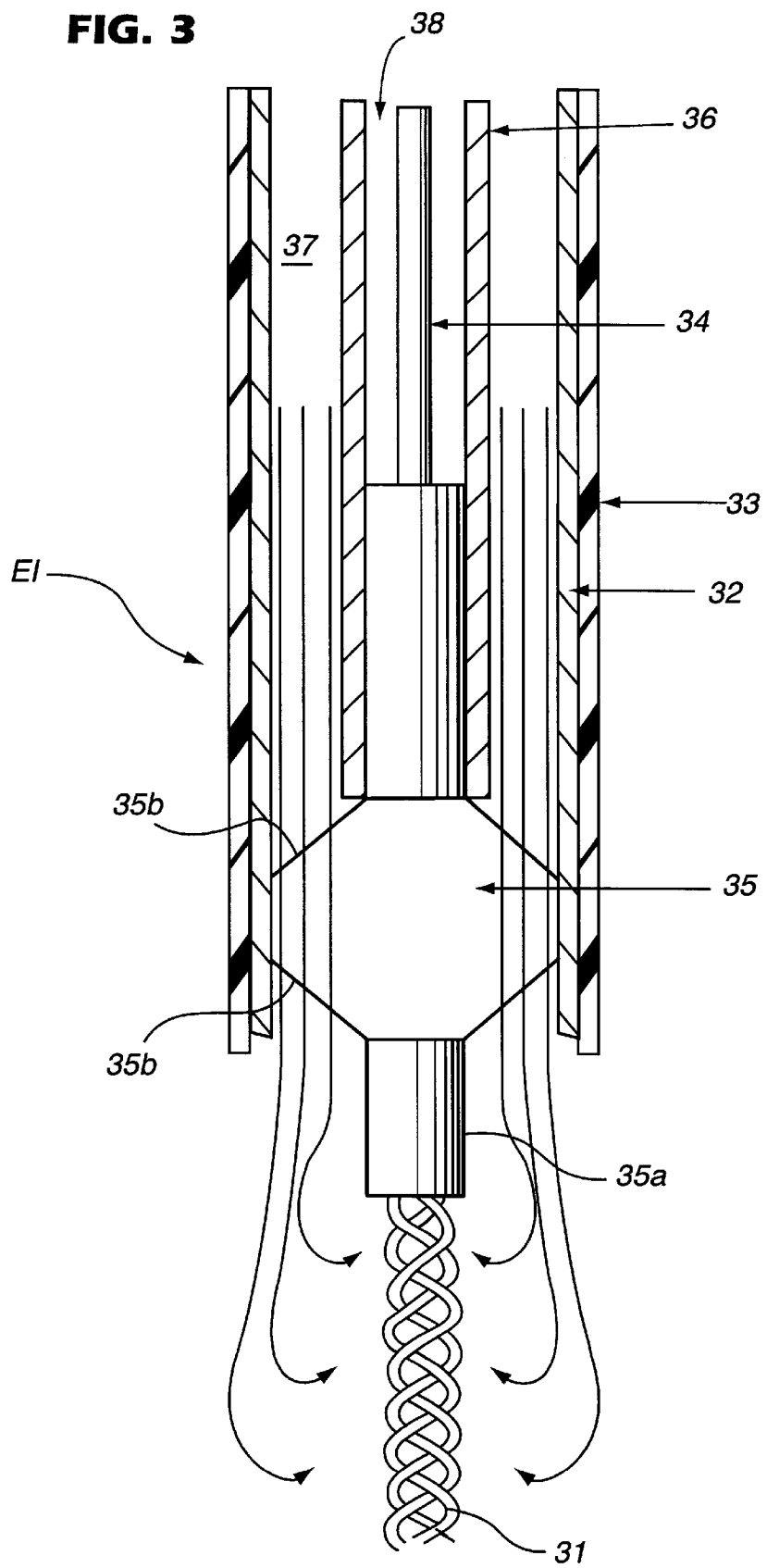
FIG. 3 is a longitudinal sectional view of the distal end of a first form of electrode unit constructed in accordance with the invention.

Each of the electrode units described below is intended to be used with an electrically conductive fluid medium such as normal saline, and each instrument has a dual-electrode structure, with the conductive medium acting as a conductor between the tissue being treated and one of the electrodes, hereinafter called the return electrode. The other electrode is applied directly to the tissue, and is hereinafter called the tissue treatment active) electrode.

Referring to the drawings, FIG. 2 shows electrosurgical apparatus including a generator 1 having an output socket 2 providing a radio frequency (RF) output for an instrument in the form of a handpiece 3 via a connection cord 4. Activation of the generator 1 may be performed from the handpiece 3 via a control connection in the cord 4, or by means of a footswitch unit 5, as shown, connected separately to the rear of the generator 1 by a footswitch connection cord 6. In the illustrated embodiment, the footswitch unit 5 has two footswitches 5a and 5b for selecting a desiccation mode and a vaporisation mode of the generator 1 respectively. The generator front panel has push buttons 7a and 7b for respectively setting desiccation and vaporisation power levels, which are indicated in a display 8. Push buttons 9a are provided as an alternative means for selection between the desiccation and vaporisation modes. The handpiece 3 mounts a detachable electrode unit E, such as the electrode units E1 to E7 to be described below.

FIG. 3 shows the distal end of the first form of electrode unit E1 for detachable fastening to the electrosurgical instrument handpiece 3. The electrode unit E1 is formed with an electrode assembly at the distal end thereof, the electrode assembly comprising a central tissue treatment (active) electrode 31 and a tubular return electrode 32. The active elect rode 31 is made of a twisted metal such as tungsten, a noble metal such as platinum, or a platinum alloy such as platinum/iridium, platinum/cobalt or platinum/tungsten, and the return electrode 32 is a stainless steel tube. The return electrode 32 is completely enveloped by an polyimide insulating sheath 33. The return electrode 32 extends the entire length of the electrosurgical instrument, and constitutes the shaft of the instrument. Thus, the return electrode 32 is maintained at a relatively low temperature due to the thermal conduction therealong.

The electrodes 31 and 32 are provided with current from the radio frequency (RF) generator 1, the return electrode 32 being directly connected to the generator and the active electrode 31 being connected via a copper conductor 34. The generator may be as described in the specification of our co-pending European Patent Application No. 96304558.8. The active electrode 31 is held centrally within the return electrode 32 by means of a ceramic insulator/spacer 35. The insulator/spacer 35 has a generally cylindrical portion 35a surrounding the junction between the active electrode 31 and the conductor 34 and the adjacent regions of these two members, and four radially-extending, equispaced wings 35b which contact the internal circumferential wall of the return electrode 32 to hold the insulator/spacer, and hence the active electrode 31, centrally within the return electrode.

A tube 36, made of an insulating material such as PTFE, is a friction fit around the proximal end of the cylindrical portion 35a of the insulator/spacer 35, and extends substantially along the entire length of the instrument. The tube 36 defines, together with the return electrode 32, a coaxial saline supply channel 37, the interior of the tube 36 defining a saline return channel 38. In use, saline is fed to the channel 37 under gravity (no pumping being required), and saline is removed via the channel 38 and apertures (not shown) in the cylindrical portion 35a of the insulator/spacer 35 by means of suction. Preferably, the suction is carried out by a low noise pump (not shown) such as a moving vane pump or a diaphragm pump, rather than by using a high speed impeller. As the tubing leading to the pump will intermittently contain small quantities of saline, a large vacuum (at least 500 m Bar) is required. However, the quantity of gas and liquid to be removed is comparatively small, and this permits the use of a moving vane or diaphragm pump, although a high volume peristaltic pump could also be used.

To circumvent the requirement for pump sterilisation, the pump operates via a disposable fluid trap (not shown) incorporating a 10 μm PTFE filter. This filter prevents both exhausted fluids and gas particulates from being drawn in by the pump and contaminating its workings and the surrounding environment.

The instrument described above is intended for use in open air or gas filled environments, in body fluids, or by insertion into tissue by the creation of a conductive fluid environment around the tip of the instrument, and it is so arranged that it is possible to create a local saline field at a distal end of the instrument. This instrument can, therefore, be used for laparoscopic applications. In use, saline is fed to the active electrode 31 via the channel 37, the saline providing a conductive medium to act as a conductive path between the tissue being treated and the return electrode 32. By varying the output of the generator 1, the instrument can be used for tissue removal via vaporisation, for cutting or for desiccation. In each case, as saline contacts the active electrode 31, it heats up until it reaches an equilibrium temperature dependent upon the power output of the generator 1 and the flow rate of the saline. In equilibrium, as fresh saline is fed via the channel 37 to the active electrode 31, the exterior temperature of the shaft is maintained at the same temperature as of that of the surrounding saline. As the insulating sheath 33 completely covers the external surface of the return electrode 32, accidental contact between the return electrode and tissue is avoided.

One of the advantages of using a low saline flow rate, is that the saline temperature can reach boiling point. However, as there is a continuous flow of saline, there is a temperature gradient rise in the saline from the return electrode 32 to the active electrode 31. This temperature gradient is important, as the hotter saline adjacent to the active electrode 31 reduces the power threshold requirement to reach vaporisation. Although the flow rate requirement can be calculated on the basis of the input power, the flexibility of the generator 1 in maintaining optimum power density means that the flow rate is non-critical. For example, if the generator 1 is set for 100 W, then the maximum flow rate is theoretically calculated as follows:

Flow rate=power/specific heat capacity
=100/4.2×75 cc/s
=0.32 cc/s
=19 cc/min

This assumes an initial saline temperature of 25° C., and a heat capacity of 4200 J/kg/° C.

Although during vaporisation saline is brought into the vapour state, the vapour is only stable around the active electrode 31. Thus, the energy absorbed by virtue of the latent heat of vaporisation can be ignored, as this energy is recovered by freshly-arriving saline.

Another important factor is that, due to the very short circuit path of the saline, the current may be regarded as flowing along a number of different paths, which, therefore, do not have the same power density. Consequently, vaporisation can occur at flow rates higher than the calculated maximum, due to the unequal power densities within the saline environment. However, the amount of vaporisation occurring along the length of the active electrode 31 will depend upon the flow rate.

As the saline is heated up by the active electrode 31, it is potentially damaging to tissue as it can cause thermal necrosis. It is important, therefore, that all the heated saline is recovered and exhausted from the patient before coming into contact with the tissue adjacent to the application site. It is for this reason that there is suction from the active electrode 31 to an exhaust reservoir (not shown). However, by ensuring that the suction occurs in excess, no saline can then escape from region of the active electrode 31 other than via the saline return channel 38. Any saline which escapes transversely beyond the exterior shaft falls away from the current path, and so is not heated. The priority is, therefore, to ensure that the hottest saline is removed. As the thermal gradient is at a maximum adjacent to the active electrode 31 this is the most appropriate exhaust point for the saline. It is for this reason that the saline is exhausted through the cylindrical portion 35a of the insulator/spacer 35.

Another important consideration in deciding the point of saline evacuation is the potential for blockage of the exhaust path. This could occur when cutting or vaporising tissue in such a way as to free small tissue particles which could easily block the exhaust. The exhaust point is, therefore, selected to be at the highest energy density point on the active electrode 31. This measure ensures that any tissue approaching the exhaust point is instantly vaporised into solution, thereby avoiding the potential for blockage.

Another significant advantage of ensuring a high degree of suction during tissue removal by vaporisation, is that any smoke which has not been absorbed by the saline is also evacuated. This is important, because smoke is capable of transmitting viable biological particles, and this could lead to infection.

As mentioned above, the power threshold for vaporisation is not well defined. If the instrument were operating in a static conductive medium, then the vaporisation threshold would be well defined by an impedance switching point where the electrode impedance suddenly rises as a result of vapour pockets forming around the active electrode 31. The threshold is normally dependent upon the dissipation mechanism of the saline. In a static environment, the dissipation mechanism is predominantly by convection currents within the saline. Under these circumstances, the power threshold for vaporisation is defined by the input power into the electrode active region being in excess of the dissipation from the saline. However, in the embodiment, described above, the saline around the active electrode 31 is continually refreshed. If it were not, then the only dissipation mechanism would be by latent heat of vaporisation, and the saline would quickly evaporate. By providing a flow, the threshold power level is increased. However, the threshold power level is dependent on the saline refresh rate at the very periphery of the active electrode 31. The refresh rate at this boundary layer can be modified by altering the surface finish of the active electrode 31. For example, if the active electrode 31 had a smooth surface, then saline would be rapidly refreshed, as a rapid flow rate would be established. However, as the active electrode 31 has an irregular finish, the refresh rate of pockets within the irregular surface is diminished. Thus, the irregular surface traps saline (or at least delays the refresh) and vapour, and so absorbs more power before being replaced. In other words, the power threshold is decreased by the irregular active electrode surface. This is a highly desirable property, as the electrode power requirement drops substantially without adversely effecting tissue performance. The threshold power is further reduced because the active electrode 31 is constructed so as to provide a capillary action. Thus, even in the vaporised state, the active electrode 31 is intermittently wetted. By ensuring that this wetting wets the entire active electrode 31 by capillary action, there is a continual source of vapour which minimises the intermittent wetting, and so further reduces the power demand.

The return electrode 32 has a smooth polished surface which has no impediment to convection currents. Consequently, the return electrode 32 does have a constantly changing saline boundary layer which is replaced at a high rate, and the return electrode has a high power threshold. Moreover, the return electrode 32 forms one edge surface of the saline feed channel 37, so that there is a turbulent flow of saline along the return electrode. This results in the boundary layer replacement being very rapid, and the electrode 32 itself being cooled by the flow. The resultant increase in the power threshold of the return electrode 32 means that vaporisation can never occur at the return electrode. Indeed, the power threshold of the return electrode 32 is increased in this way so that it is considerably in excess of the maximum available power. This ensures that, even if the return electrode 32 is partially obscured, or the flow of saline impeded, the power threshold at the return electrode will never be reached. As the power threshold for vaporisation at the return electrode 32 cannot be reached, there is no risk of tissue being vaporised by the return electrode. Collateral tissue damage is, therefore, avoided. Moreover, as the saline exhaust channel 38 is inside the return electrode 32, the hottest saline is removed efficiently, thereby precluding tissue damage by plumes of heated saline leaving the active electrode 31.

By varying the output of the generator 1, the electrode unit El can also be used for desiccation (coagulation). In this case, the generator 1 is controlled so that small vapour bubbles form on the surface of the active electrode 31, but insufficient vapour is produced to provide a vapour bubble (pocket) surrounding the active tip of the electrode, the vapour bubble being essential for tissue removal by vaporisation.

The generator 1 is controlled in such a manner that it has respective output ranges for tissue desiccation and for tissue removal by vaporisation. The former range is from 150 volts to 200 volts, and the latter range is from 250 volts to 600 volts, the voltages being peak voltages. In the vaporisation mode, the generator 1 is controlled in such a manner as to prevent the active electrode 31 overheating. This requires a reduction in the output voltage of the generator 1 once a vapour pocket has been established. The generator 1 and its control means are described in greater detail in the specification of our co-pending European Patent Application 96304558.8.

The coagulation from this electrode is vastly superior to any conventional bipolar electrode. The reasons are two fold. Firstly, the coagulation mechanism is not merely by electrical current in the tissue, but is also due to the heated saline. Secondly, under normal circumstances, the weakest link in providing electrical power to the tissue is the electrode interface, as this is the point of highest power density, and so imposes a power limit. If too high a power level is attempted, the tissue at the interface quickly desiccates, far faster than the larger cross-section of tissue forming the remaining circuit. If a lower power is selected, the interface can dissipate the temperature rise by mechanisms other than vaporisation. Consequently, the interface remains intact longer, and so a greater depth of effect can be achieved. In this embodiment, the electrical interface is much stronger by virtue of the saline, and it is not possible completely to desiccate the target tissue. Thus, power can be delivered at a higher rate and for a longer period, resulting in a depth of effect which is purely time and power related.

Vaporisation threshold control is an important aspect of such a multi-functional active electrode, the active electrode area being maximised for desiccation, whilst still being capable of vaporisation or cutting functions by retaining the vapour pocket and heated saline in the interstices of the active electrode.

As mentioned above, a fundamental feature of the design of a bipolar electrosurgical instrument is the ratio of the contact areas of the return electrode and of the active electrode. This ratio should be high for vaporisation and low for desiccation. A balance must, therefore, be struck for multi-functional electrodes. The electrode unit E1 achieves this balance by minimising the ratio to ensure efficient desiccation, and by providing vaporisation threshold control to ensure efficient vaporisation.

Figure 4:
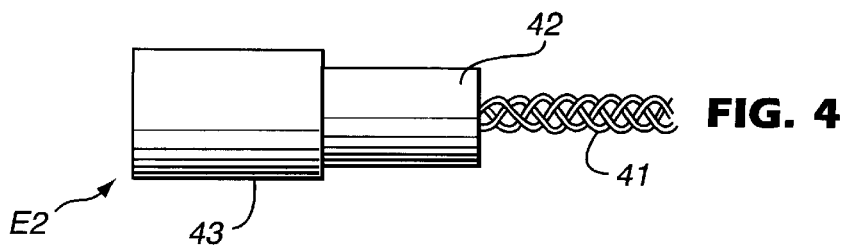
FIG. 4 is a diagrammatic side elevation of the electrode assembly of a second form of electrode unit constructed in accordance with the invention.

FIG. 4 shows the electrode assembly of the second form of electrode unit E2. This unit E2 has a shaft (not shown) for detachably fastening the unit to the electrosurgical instrument handpiece 3. The electrode assembly is positioned at the distal end of the shaft, means (not shown) being provided at the other end of the shaft for connecting the electrode assembly to the handpiece 3 both mechanically and electrically.

The electrode assembly includes a central, tissue contact (active) electrode 41 which is exposed at the extreme distal end of the instrument. The active electrode 41 is made of twisted strands of a metal such a tungsten, or a noble metal such as platinum, or a platinum alloy such as platinum cobalt, platinum/iridium or platinum/tungsten. The active electrode 41 is electrically connected to the RF generator by a central conductor (not shown). An insulating sleeve 42 surrounds the active electrode 41 and the inner conductor, the distal end of the insulating sleeve being exposed proximally of the exposed part of the electrode 41. The sleeve 42 is made of a ceramic material, silicone rubber or glass. A return electrode 43 surrounds the sleeve 41, the return electrode being in the form of a stainless steel tube. The return electrode 43 is constituted by the distal end portion of the shaft of the instrument, and is electrically connected to the RF generator. An outer insulating polyamide coating (not shown) surrounds that portion of the shaft adjacent to the return electrode 43.

The electrode unit E2 of FIG. 4 is intended for tissue removal by a vaporisation within a distension medium in the form of an electrically conductive liquid such as saline. In this case, the power threshold required to reach vaporisation is dependent on the power dissipation capability of the active electrode 41 and the flow characteristics around it. As the electrode assembly is immersed in saline, power dissipation is by electrical conversion to heat. The heated saline rises as a plume from the active electrode 41 by the action of convection. Under these circumstances, the power threshold of vaporisation is dependent on the maximum rate of convection from the active electrode.

The highest power density exists at the surface boundary of the active electrode 41. Power density falls off at a rate proportional to $1/d^2$ where d is the distance away from the active electrode 41. Therefore, it is the saline at the surface of the electrode 41 which defines the power threshold. The rate of saline replacement by convection and conduction losses at this point defines the power threshold. As soon as this boundary layer vaporises, then the electrode 41 becomes stable in vaporisation with a lower power level.

The irregular surface of the active electrode 41 traps saline, and so absorbs more power before being replaced. A highly polished active electrode would have a constantly changing saline boundary layer, due to the convection currents "washing" its surface. In this case, the boundary layer would be replaced at a high rate, so there would be a high power threshold. The irregular surface of the active electrode 41, however, results in the trapping of saline (and vapour) so that the saline boundary layer changes at a low rate. Thus, the irregular surface of the active electrode 41 defines a number of peaks and troughs. The saline at the boundary layer of the peaks will be replaced readily by the convection currents. However, the convection of saline in the troughs will be impeded. Thus, the saline in the troughs will not be replaced as quickly, and so will absorb more power before being replaced. In other words, the power threshold is decreased by the irregular surface of the active electrode 41. As with the embodiment of FIG. 2, this is desirable as the electrode power requirement drops substantially without adversely affecting tissue performance. The threshold power is further reduced because the active electrode 41 is constructed so as to provide a capillary action. Thus, even in a vaporised state, the active electrode 41 is intermittently wetted. By ensuring that this wetting wets the entire active electrode 41 by capillary action, there is a continual source of vapour which minimises the intermittent wetting, and so further reduces the power demand.

In the electrode unit E2 of FIG. 4, the strands are shown loosely twisted, so that adjacent strands touch each other either at spaced positions or not at all. Such a structure leaves a series of openings in the electrode that connect to a central axial cavity within the electrode structure lying along the longitudinal axis of the electrode. To prevent the electrode from fraying at its tip, the distal ends of the strands may be connected together, such as by welding or another fusing method.

Figure 5:
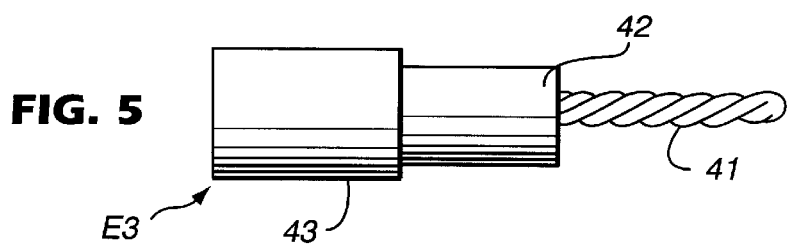
FIG. 5 is a diagrammatic side elevation of a modified electrode assembly similar to that of FIG. 4.

Referring to FIG. 5, in a variation of the embodiment of FIG. 4, an alternative electrode unit E3 has a plurality of conductive strands which are twisted or otherwise interlaced tightly about each other, so that adjacent strands press tightly against each other, causing any cavities lying along the electrode longitudinal axis within the twisted structure to be small or non-existent. In this embodiment, substantially all the pockets for trapping conductive fluid are located at the outer surface of the electrode, in and along the joins between adjacent strands. The preferred material for the strands is an alloy of platinum or iridium. The tightly-wound configuration provides a more rigid structure than that of electrode unit E2 shown in FIG. 4. Again, the strands are welded together at the extreme distal end of the electrode.

In a further alternative electrode structure, not shown in the drawings, the central, tissue treatment (active) electrode 41 may be formed from a single length of conductive material with helical ridges formed in its outer surface, either created by moulding, machining, or by twisting a piece of the material (preferably of non-circular cross-section) about its longitudinal axis to cause spiralling ridges about the outer surface. As before, the ridges create pockets therebetween. Formation of spiralling ridges from a non-circular cross-section length of material may be performed by twisting the material so that the ridges are formed in the same way as ridges are formed when an elastic band is twisted about its own axis.

The above described alternatives to the twisted and interlaced structure of FIG. 4 may also be used in the embodiment of FIG. 3.

Figure 6:
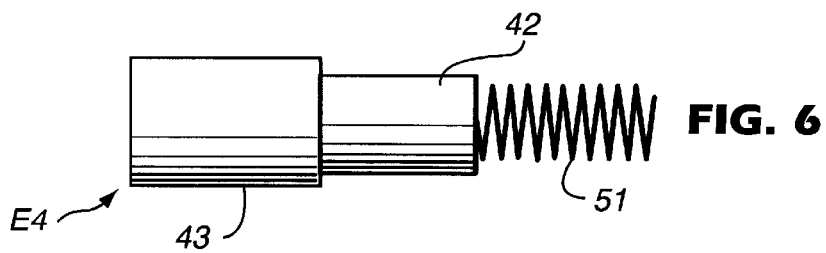
FIG. 6 is a diagrammatic side elevation of the electrode assembly of a third form of electrode unit constructed in accordance with the invention.
Figure 7:
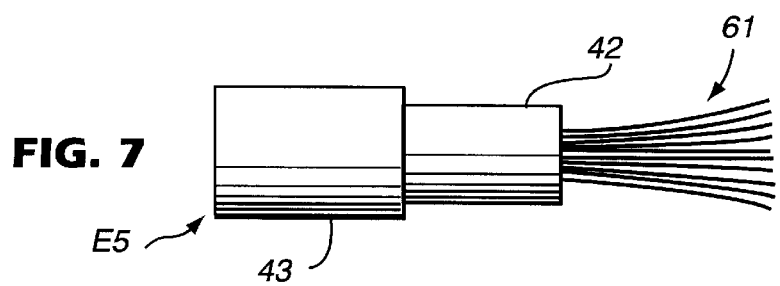
FIG. 7 is a diagrammatic side elevation of the electrode assembly of a fourth form of electrode unit constructed in accordance with the invention.
Figure 8:
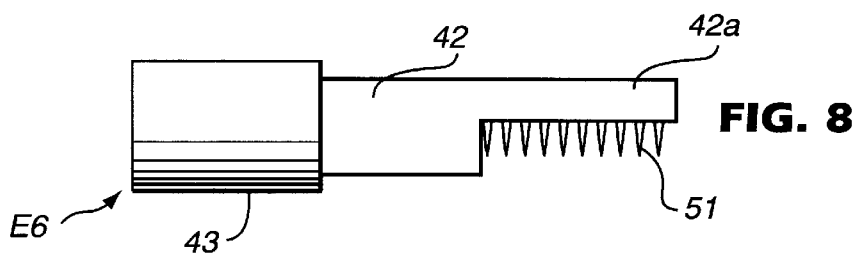
FIG. 8 is a diagrammatic side elevation of the electrode assembly of a fifth form of electrode unit constructed in accordance with the invention.

FIGS. 6 to 8 show modified versions E4 to E6 of the electrode units E2 and E3 of FIGS. 4 and 5, so like reference numerals will be used for like parts, and only the modifications will be described in detail. Thus, the electrode unit E4 of FIG. 6 includes an active electrode 51 in the form of a helical coil, the active electrode being made of tungsten, a noble metal such as platinum, or of a platinum alloy such as platinum/iridium, platinum/cobalt or platinum/tungsten. In use, saline is trapped between adjacent turns of the coil, so here again the saline boundary layer changes at a low rate, thereby ensuring that the active electrode 51 has a low power threshold. The active electrode 51 has the additional advantage that saline is trapped within the coil itself, thereby leading to a further reduction in the replacement rate of saline at the boundary layer, and a consequent further reduction in the power threshold.

FIG. 7 shows an electrode unit E5 having an active electrode 61 in the form of a brush constituted by a plurality of filaments made of tungsten, a noble metal such as platinum, or a platinum alloy such as platinum/iridium, platinum/cobalt or platinum/tungsten. In use, saline is trapped within the strands of the filaments, once again leading to a reduction in the replacement of saline at the boundary layer, and a reduction in the power threshold. The filaments of the brush electrode 61 also provide a capillary action, further reducing the power threshold.

The electrode unit E6 of the embodiment of FIG. 8 is similar to that of FIG. 6, having an active electrode 51 is in the form of a coil made of tungsten, a noble metal such as platinum, or a platinum alloy such as platinum/iridium, platinum/cobalt or platinum/tungsten. In this embodiment, however, the insulating sleeve 42 is formed with an arcuate extension 42a which constitutes a shroud. The inner surface of the shroud 42a closely overlies the turns of the coil electrode 51 over about half its circumference. The shroud 42a does, therefore, impede convection current flow, thereby increasing the ability of the electrode assembly to trap saline, and so leads to a further decrease in the power threshold. This electrode assembly benefits from a secondary mechanism. Thus, when in the vaporising state, tissue destruction yields gaseous products. The shroud 42a captures these gaseous products, and so excludes conduction by virtue of the insulating properties of these gaseous products.

FIG. 9 shows a further form of electrode unit E7 having an active electrode 71 in the form of a roller ball. The roller ball electrode 71 is made of stainless steel, and is rotatably supported on an arm 72 made of an electrically-conductive material such as copper. A generally hemispherical shroud 73 is fixed to the arm 72 so as to closely surround about half of the area of the ball electrode 71. The shroud 73 is made of an insulating material such as ceramic material, silicone rubber or glass. A return electrode 74 made of stainless steel is mounted on that side of the shroud 73 remote from the ball electrode 71. Here again, the shroud 73 traps saline between its inner surface and the outer surface of the roller ball electrode 71, so the power threshold of the active electrode is reduced. The shroud 73 also traps the products of vaporisation to reduce the effective size of the large active electrode 71. Moreover, by excluding a direct return path through the saline, the return: active area ratio is effectively increased. This feature reduces the amount of power required to support vaporisation, and enables the use of a much larger active electrode 71 than would otherwise be possible. Another advantage of the shroud 73 is that it preserves the environment in the immediate region of the active electrode 71 from disturbances which otherwise would be created by the flow of saline.

Figure 10:
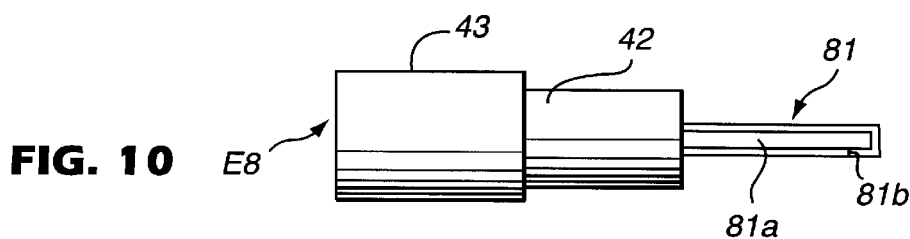
FIG. 10 is a diagrammatic side elevation of the electrode assembly of a seventh form of electrode unit constructed in accordance with the invention.

FIG. 10 shows another form of electrode unit E8 having an active electrode 81 which is constituted by a needle electrode 81a made of tungsten, a noble metal such as platinum, or a platinum alloy such as platinum/iridium, platinum/cobalt or platinum/tungsten coated with a conductive ceramic material 81b. The coating 81b increases the power dissipation at the saline boundary layer, by increasing the local power density within the active electrode 81. This results in an increase in the interfacing impedance between the electrode 81 and the saline. This increase in power dissipation leads to a reduction in the power threshold of the electrode 81. This method of reducing the power threshold of an active electrode 81 is particularly useful for situations where active electrode is necessarily very small due to the limitations imposed by certain operational requirements. Obviously, the electrode 81a could be coated with any other highly resistive inert material, such as a highly resistive metal plating which is capable of withstanding the elevated temperatures associated with the vaporisation of tissue. Alternatively, the local power density of the electrode 81a could be increased by spraying it with a porous insulating material such as a ceramic material, the spraying being such as to produce spots of insulation on a conductive surface.

The return electrode of each of the embodiments of FIGS. 4 to 10 has a smooth polished surface which has no impediment to convection currents. As with the embodiment of FIG. 2, therefore, each of these return electrodes has a high power threshold for vaporisation, so that there is no risk of tissue being vaporised by the return electrode, and no risk of collateral tissue damage. The electrode assembly of each of these embodiments could be positioned adjacent to the saline supply port of an endoscope so that saline will flow over the return electrode to provide a turbulent flow of saline along that electrode. This would result in the boundary layer replacement at the return electrode being very rapid, and further increase the power threshold of the return electrode.

As mentioned above, multifunctional electrode units require vaporisation threshold control, and a minimum for the ratio of the contact areas of the return electrode and the active electrode. The minimum ratio depends on four important criteria, namely:

1. The intrinsic impedance of the target tissue;
2. The volume of the body cavity;
3. The configuration of the active electrode.
4. The maximum output power from RF generator.

The configuration of the active electrode obviously influences the ratio, with cylindrical forms representing the lowest ratio for a given length, but the other factors relate to the ability of the electrode to retain the vapour bubble. The filaments of the brush-type electrodes retain vapour bubbles, which helps maintain the vaporisation condition. As a result, the ratio for this type of electrode can be lowest of the multifunctional electrodes; and, when combined with application to tissue with high impedance, the ratio is similar to that for desiccate functions, that is in the region of 1:1 to 2:1. With solid electrode forms, however, the transition and maintenance of the vaporisation condition at similar ratios requires very high power levels (greater than 150 w at 1.5 mm diameter) for a given electrode size. As a result, the ratio must be elevated for these forms to the region of 2:1 to 3:1. Changing the exterior surface with a variety of grooves or cuts, or by using coiled wire to produce a similar form, assists vaporisation performance by stimulating the vapour pocket retention of the brush-type electrodes, thereby allowing a reduction in the ratio.

An arthroscopic electrode may be characterised as short (100–140 mm), rigid, and having a working diameter up to 4 mm. If can be introduced through a stab incision into a joint cavity (with or without a cannula) using the triangulation technique. It is operated with a motion which commonly moves the electrode between the 9 o'clock and 3 o'clock positions on the arthroscopic image. As a result, the tissue to be treated is commonly approached at a shallow working angle with respect to the axis of the electrode. The active electrode, therefore, needs to include a range of end-effect to side-effect properties. In certain circumstances, an end-effect is desirable, particularly as an end-effect is very difficult to obtaining using a shaver device wherein the centre of rotation represents the desired point of application. The tissue to be treated (such as meniscal cartilage) is commonly dense and of a high electrical impedance with a free edge of the cartilage representing the common site of injury where treatment is required. The electrode units E1, E2, E3, E4, E5 and E8 are end-effect electrode units suitable for arthroscopic use.

Either extensions or side-effect configurations of the insulator material assist with engagement, and prevent unwanted effects occurring in adjacent structures - usually the articular surfaces of the femur and tibia. In addition, the extension or side-effect electrode forms (of FIGS. 8 and 9) also assist in retaining the vapour pocket, and prevent cooling of the saline in the immediate vicinity of the active electrode by the flow of saline irrigant commonly from the endoscope.

The risk of heating distension fluid within the joint cavity occurs primarily during power application to reach the vaporisation threshold. Once the threshold has been reached, power requirements typically fall by 30–50%. Reducing the ratio increases the power requirement to reach the threshold so that, despite the high impedance of the target tissue, it is undesirable to reduce the ratio to the lowest value capable of supporting vaporisation. The feature of vaporisation threshold control retains vapour pockets and heated saline in the interstices of the electrode, and configures the insulator to reduce the effect of irrigant flow, thereby assisting in reducing the power required to establish vaporisation and hence the risk of unwanted heating.

By way of example, the coiled wire-form electrode of FIG. 6 entraps vapour products, as does the electrode of FIG. 8 (a side-effect form with the added feature of the insulator shrouding the non-contact region of the active electrode). The addition of the insulator shrouding feature can halve the power required to reach the vaporisation threshold.

Figure 11:
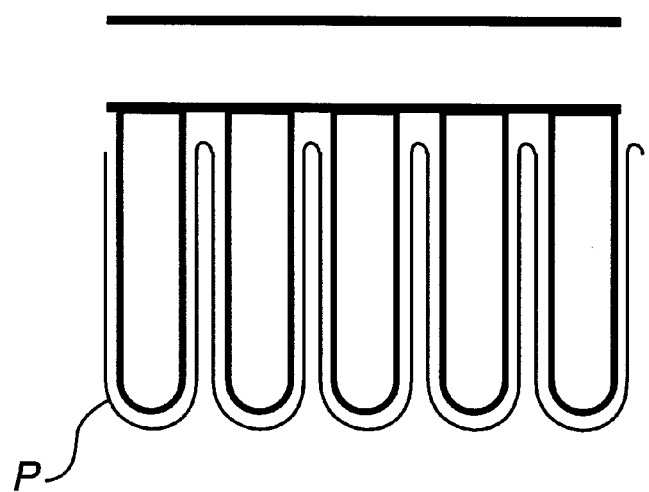
FIGS. 11 and 12 are schematic side elevations of the distal end portion of an electrode assembly similar to that of FIG. 7, showing different stages in the formation of a vapour pocket around conductive electrode filaments.
Figure 12:
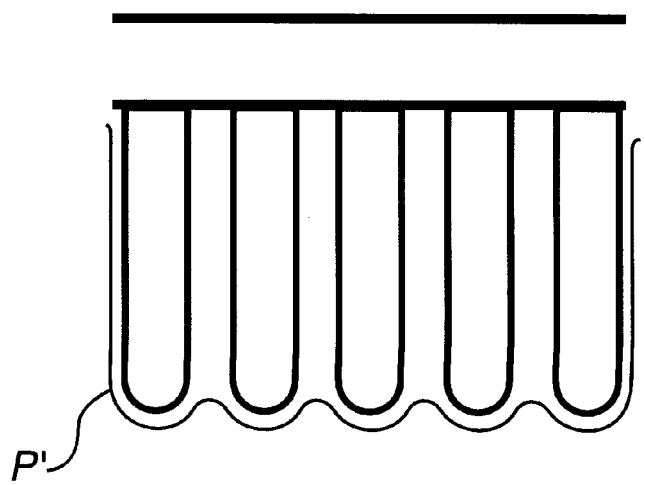

Typically, in arthroscopic use, the primary function comprises rapid debulking of dense, avascular tissue. The volume of tissue removed can be increased for a given size of electrode by a combination of the vaporisation threshold control feature and by increasing the output voltage from the RF generator 1. FIG. 11 shows a schematic of the brush-type electrode of FIG. 8, wherein the vapour threshold is exceeded, and a vapour pocket, indicated by the reference P, is established around each of the filaments. When applied to tissue, particularly firm, dense tissue such as that comprising meniscal cartilage, the result will be vaporisation of a series of grooves in the tissue corresponding each of the filaments. Increasing the RF output voltage will increase the size of the vapour pockets around each of the filaments which, because of the retention will reach the stage, shown in FIG. 12, where they merge to form a contiguous vapour pocket, indicated by the reference P', so that tissue which may otherwise have passed between the filaments is also vaporised.

Our co-pending European Patent Application No. 96304558.8 discloses discrimination between desiccation and vaporisation output functions. It also discloses that a blended function can be created by constantly alternating between these output states. Vaporisation threshold control is particularly advantageous in these circumstances, as the hot saline created by the desiccate output phase is retained in proximity to the active electrode such that the vaporisation threshold is rapidly exceeded during the vaporisation cycle. This is useful as a method to achieve simultaneous desiccation when detaching muscle from bony attachments, such as is performed in an acromioplasty of the shoulder joint, or when debulking diseased tissue with a vascular component such as synovium.

The embodiment of FIG. 9 is particularly useful with a resectoscope to perform electrosurgical vaporisation of the prostate (EVAP). This particular configuration comprises a roller bar (cylindrical) active electrode 71, typically 2.4 to 3 mm in diameter by 3 to 4 mm in width. It is evident that the return electrode 74 could be mounted in an axially-separated arrangement on the shaft 72. Under these circumstances, however, the size of the active electrode 71, and the exposure of the complete surface area to the conductive environment as well as the cooling effect of irrigant flow over the electrode, would require a very high power to reach the vaporisation threshold.

It will be appreciated that the electrode 71 can be grooved or ridged so as to further reduce the vaporisation threshold. Similarly, the side-effect active electrode of FIG. 8 which could be axially or transversely mounted with respect to the axis of the resectoscope), could be substituted for the electrode assembly of FIG. 9. In this case, the active electrode would not provide a mechanical rolling function.

This instrument can also be used to perform electrosurgical vaporisation of soft tissue tumours, such as a prostatic adenoma, without use of a dispersive return plate in a conductive fluid environment. It can also be applied to fibroids using a resectoscope in the uterine cavity.

The electrosurgical instruments described above also have irrigated electrode applications. Thus, each utilises a method of creating a localised saline working environment as a means of completing the electrical circuit of axially separated active and return electrodes to perform tissue vaporisation, cutting and desiccation in a gas or air filled body cavity whether of natural origin or created surgically, or at a tissue surface of the body whether of natural origin or created surgically.

More specifically, each such instrument utilises a method of removing tissue by vaporisation wherein the products of vaporisation are aspirated from the site of application by suction through, or adjacent to, the active electrode assembly. Diseased tissue can be also removed by vaporisation from natural body cavities such as sinuses, nasal cavities and the oropharynx. Similarly, diseased tissue can be removed by vaporisation from the abdominal cavity under gaseous distension.

Such an instrument can also be used to create the surgical access to an interstitial site where the tissue to be treated is lying deep to the tissue surface.

What is claimed is:

1. A method of operating an electrosurgical apparatus having at least a tissue desiccation mode and a tissue vaporization mode, the apparatus having a radio frequency generator coupled to an electrode assembly for the treatment of tissue in the presence of an electrically-conductive fluid medium, the electrode assembly comprising a tissue treatment electrode and a return electrode which is electrically insulated from the tissue treatment electrode by means of an insulation member, the tissue treatment electrode being exposed at the distal end portion of the assembly, and the return electrode having a fluid contact surface spaced proximally from the exposed end of the tissue electrode by the insulation member, the method comprising the steps of:

controlling the output power of the radio frequency generator to lie within a first output range to operate the apparatus in the tissue desiccation mode and, alternatively, to lie within a second output range to operate the apparatus in the tissue vaporization mode, the first output range being such that the power supplied to the electrode assembly maintains the conductive fluid adjacent to the tissue treatment electrode substantially at boiling point for tissue desiccation without creating a vapour pocket surrounding the tissue treatment electrode, and the second output range is such that the output power supplied to the electrode assembly for vaporization of tissue is such as to maintain a vapour pocket surrounding the tissue treatment electrode; and reducing the power threshold for vaporization at the tissue treatment electrode when the output power of the radio frequency generator is in the second output range.

2. A method as claimed in claim 1, wherein the tissue treatment electrode is constructed to define pockets for trapping electrically-conductive fluid and vapour, thereby increasing power absorption at the tissue treatment electrode and so decreasing the vaporisation power threshold.

3. A method as claimed in claim 1, wherein the tissue treatment electrode is made from an electrically-conductive material and is coated with a resistive inert material whereby, when the output power of the radio frequency generator is in the second output range, the local power density within the tissue treatment electrode increases, thereby decreasing the vaporisation power threshold.

4. A method as claimed in claim 2, wherein the first output range is from about 150 volts to 200 volts and the second output range is from about 250 volts to 600 volts, the voltages being peak voltages.

5. An electrosurgical method comprising the steps of:

providing an electrosurgical apparatus comprising a radio frequency generator coupled to an electrode assembly comprising a tissue treatment electrode and a return electrode, the tissue treatment electrode being exposed at the distal end portion of the assembly;

introducing the electrode assembly into a selected operation site with the tissue treatment electrode adjacent to the tissue to be treated, and with the tissue and the tissue treatment electrode immersed in a conductive liquid;

activating the generator;

applying sufficient radio frequency power to the electrode assembly to vaporize the conductive liquid surrounding the tissue treatment electrode to maintain a vapour pocket surrounding the tissue treatment electrode; and reducing the power threshold for vaporization at the tissue treatment electrode by providing the tissue treatment electrode with a coating that increases power dissipation at a boundary layer of the conductive liquid by increasing local power density within the tissue treatment electrode.

6. A method as claimed in claim 5, wherein the return electrode is spaced proximally with respect to the tissue treatment electrode, and wherein the electrode assembly is introduced into the selected operation site such that the tissue treatment electrode is positioned at least adjacent to the tissue to be treated, with the vapour pocket in contact with the tissue, and with the return electrode immersed in the conductive liquid, the electrode structure being manipulated to achieve at least vaporisation of the tissue.

7. The electrosurgical method of claim 5 wherein the coating is a conductive ceramic material.

8. The electrosurgical method of claim 8 wherein the increase in local power density increases an interfacing impedance between the tissue treatment electrode and the conductive liquid.

9. The method of claim 9 wherein the increase in power dissipation leads to a reduction in the power threshold of the tissue treatment electrode.

* * * * *